(12) United States Patent
Hochstetler et al.

(10) Patent No.: US 11,835,481 B2
(45) Date of Patent: Dec. 5, 2023

(54) PHYSICAL VAPOR DEPOSITED BIOSENSOR COMPONENTS

(71) Applicant: Eastman Chemical Company, Kingsport, TN (US)

(72) Inventors: Spencer Erich Hochstetler, Kingsport, TN (US); Senthil Nathan Sambandam, Fairfax, VA (US); Dennis Lee Ashford, II, Johnson City, TN (US)

(73) Assignee: Eastman Chemical Company, Kingsport, TN (US)

( * ) Notice: Subject to any disclaimer, the term of this patent is extended or adjusted under 35 U.S.C. 154(b) by 608 days.

(21) Appl. No.: 16/305,594

(22) PCT Filed: Jun. 1, 2017

(86) PCT No.: PCT/US2017/035353
§ 371 (c)(1),
(2) Date: Nov. 29, 2018

(87) PCT Pub. No.: WO2017/218197
PCT Pub. Date: Dec. 21, 2017

(65) Prior Publication Data
US 2020/0271611 A1   Aug. 27, 2020

Related U.S. Application Data

(60) Provisional application No. 62/350,476, filed on Jun. 15, 2016.

(51) Int. Cl.
*G01N 27/327* (2006.01)
*G01N 33/543* (2006.01)
(Continued)

(52) U.S. Cl.
CPC ......... *G01N 27/3272* (2013.01); *C12Q 1/006* (2013.01); *C23C 14/205* (2013.01);
(Continued)

(58) Field of Classification Search
CPC .. C12Q 1/006; G01N 27/3272; G01N 27/327; G01N 27/40; G01N 27/48;
(Continued)

(56) References Cited

U.S. PATENT DOCUMENTS 3,264,074 A   8/1966 Jones et al.
4,752,360 A   6/1988 Jasinski
(Continued)

FOREIGN PATENT DOCUMENTS

CN   1779455 A   5/2006
CN   101393160 A   3/2009
(Continued)

OTHER PUBLICATIONS

Nickel & High Temperature Alloys chart (Year: 2016).*
(Continued)

*Primary Examiner* — Gurpreet Kaur
(74) *Attorney, Agent, or Firm* — Michael K. Carrier; Robert C. Morriss

(57) ABSTRACT

A biosensor component is provided that provides enhanced characteristics for use in biosensors, such as blood glucose sensors. The biosensor component comprises a substrate and a conductive layer coated on the substrate. The conductive layer includes nickel, chromium, and iron, such that a combined weight percent of the nickel and chromium in the conductive layer is in the range of 80 to less than 95 weight percent, and the weight percent of iron in the conductive layer is greater than 5 weight percent and less than 12 weight percent.

20 Claims, 6 Drawing Sheets

(51) Int. Cl.
*C12Q 1/00* (2006.01)
*C23C 14/20* (2006.01)
*C23C 14/34* (2006.01)
*C23C 14/56* (2006.01)

(52) U.S. Cl.
CPC ............ *C23C 14/34* (2013.01); *C23C 14/562* (2013.01); *G01N 33/5438* (2013.01)

(58) Field of Classification Search
CPC ........ G01N 27/26; G01N 27/10; G01N 27/06; G01N 33/5438; G01N 33/553; A61B 5/14532; A61B 5/05; A61B 5/1486
See application file for complete search history.

(56) References Cited

U.S. PATENT DOCUMENTS

| | | | |
|---|---|---|---|
| 5,227,211 A | 7/1993 | Eltoukhy et al. |
| 5,429,895 A | 7/1995 | Lian et al. |
| 5,484,517 A | 1/1996 | Hopson, Jr. |
| 5,837,354 A | 11/1998 | Ogisu et al. |
| 6,013,170 A | 1/2000 | Meade |
| 6,096,426 A | 8/2000 | Moker'l |
| 6,103,033 A | 8/2000 | Say et al. |
| 6,171,714 B1 | 1/2001 | Bergkessel et al. |
| 6,187,479 B1 | 2/2001 | Liu |
| 6,332,900 B1 | 12/2001 | Muffoletto et al. |
| 6,352,781 B1 | 3/2002 | Lohwasser et al. |
| 6,388,366 B1 | 5/2002 | Pryor |
| 6,468,657 B1 | 10/2002 | Hou et al. |
| 6,484,045 B1 | 11/2002 | Holker et al. |
| 6,572,936 B1 | 6/2003 | Domoto et al. |
| 6,758,957 B1 | 7/2004 | Zhou et al. |
| 6,821,624 B2 | 11/2004 | Utsumi et al. |
| 6,824,974 B2 | 11/2004 | Pisharody et al. |
| 6,828,040 B2 | 12/2004 | Cunningham et al. |
| 6,855,243 B2 | 2/2005 | Khan |
| 6,859,310 B2 | 2/2005 | Simpson et al. |
| 6,869,676 B2 | 3/2005 | Burger et al. |
| 6,921,469 B2 | 7/2005 | Larsen |
| 7,018,523 B2 | 3/2006 | Meade |
| 7,057,805 B2 | 6/2006 | Phillips et al. |
| 7,063,776 B2 | 6/2006 | Huang |
| 7,139,162 B2 | 11/2006 | Michel et al. |
| 7,216,661 B2 | 5/2007 | Welty et al. |
| 7,416,786 B2 | 8/2008 | Oda et al. |
| 7,465,597 B2 | 12/2008 | Wegner et al. |
| 7,510,786 B2 | 3/2009 | Veerasamy et al. |
| 7,556,724 B2 | 7/2009 | Huang |
| 7,563,346 B2 | 7/2009 | Chen |
| 7,563,509 B2 | 7/2009 | Chen |
| 7,611,751 B2 | 11/2009 | Elers |
| 7,662,880 B2 | 2/2010 | Xia et al. |
| 7,688,167 B2 | 3/2010 | Paranjpye et al. |
| 7,781,322 B2 | 8/2010 | Ku et al. |
| 7,824,620 B2 | 11/2010 | Bau et al. |
| 7,858,147 B2 | 12/2010 | Wu et al. |
| 7,919,151 B2 | 4/2011 | Deng et al. |
| 7,939,172 B2 | 5/2011 | Gorokhovsky et al. |
| 8,192,820 B2 | 6/2012 | Asplund et al. |
| 8,287,719 B2 | 10/2012 | Bhattacharya |
| 8,309,362 B2 | 11/2012 | Palleschi et al. |
| 8,372,524 B2 | 2/2013 | Chang et al. |
| 8,378,335 B2 | 2/2013 | Yamazaki et al. |
| 8,420,363 B2 | 4/2013 | Wang et al. |
| 8,424,763 B2 | 4/2013 | Charlton et al. |
| 8,440,563 B2 | 5/2013 | Matsumoto et al. |
| 8,493,711 B2 | 7/2013 | Seymour |
| 8,503,162 B2 | 8/2013 | Seymour |
| 8,574,679 B2 | 11/2013 | Kawabata |
| 8,603,308 B2 | 12/2013 | Bhullar et al. |
| 8,603,608 B2 | 12/2013 | Shin et al. |
| 8,603,825 B2 | 12/2013 | Chua et al. |
| 8,613,822 B2 | 12/2013 | Van Nutt et al. |
| 8,623,153 B2 | 1/2014 | Pruneri et al. |
| 8,685,802 B2 | 4/2014 | Kelber et al. |
| 8,795,856 B2 | 8/2014 | Kaiju et al. |
| 8,809,843 B2 | 8/2014 | McKone et al. |
| 8,974,983 B2 | 3/2015 | Himeno et al. |
| 8,980,073 B2 | 3/2015 | Pourmand et al. |
| 9,105,378 B2 | 8/2015 | Kim et al. |
| 9,122,336 B1 | 9/2015 | Lai |
| 9,159,924 B2 | 10/2015 | Lee et al. |
| 9,222,909 B2 | 12/2015 | Watanabe et al. |
| 9,343,533 B2 | 5/2016 | Seacrist et al. |
| 9,418,796 B2 | 8/2016 | Yoshimura et al. |
| 9,506,890 B2 | 11/2016 | Hochstetler et al. |
| 9,567,680 B2 | 2/2017 | Kim et al. |
| 9,643,842 B2 | 5/2017 | Tan et al. |
| 10,569,330 B2 | 2/2020 | King et al. |
| 10,808,273 B2 | 10/2020 | Goodwin et al. |
| 11,624,723 B2 | 4/2023 | Hochstetler et al. |
| 11,630,075 B2 | 4/2023 | Hochstetler et al. |
| 2002/0044405 A1 | 4/2002 | Muffoletto et al. |
| 2004/0039928 A1 | 2/2004 | Elbe et al. |
| 2004/0086717 A1 | 5/2004 | Sasaki et al. |
| 2004/0118705 A1 | 6/2004 | Khan |
| 2005/0012115 A1 | 1/2005 | Grueger et al. |
| 2005/0199585 A1 | 9/2005 | Wang et al. |
| 2005/0284758 A1 | 12/2005 | Funke et al. |
| 2006/0068392 A1 | 3/2006 | Kimura et al. |
| 2006/0175199 A1 | 8/2006 | Huang |
| 2006/0269826 A1 | 11/2006 | Katz et al. |
| 2007/0193882 A1 | 8/2007 | Dai et al. |
| 2007/0290591 A1 | 12/2007 | Lykowski et al. |
| 2008/0083618 A1 | 4/2008 | Neel et al. |
| 2009/0071837 A1 | 3/2009 | Fredenberg et al. |
| 2010/0129615 A1 | 5/2010 | Chizik et al. |
| 2010/0181869 A1 | 7/2010 | Pereira da Cunha et al. |
| 2010/0213079 A1* | 8/2010 | Willis ................ A61B 5/14865 205/775 |
| 2010/0291464 A1 | 11/2010 | Elhamid et al. |
| 2011/0272295 A1 | 11/2011 | Lee et al. |
| 2012/0118735 A1 | 5/2012 | Kim et al. |
| 2012/0164434 A1 | 6/2012 | Ramadas et al. |
| 2012/0222958 A1 | 9/2012 | Pourmand et al. |
| 2012/0299175 A1 | 11/2012 | Tran |
| 2012/0301816 A1 | 11/2012 | Lee |
| 2012/0328906 A1 | 12/2012 | Kwon et al. |
| 2013/0052475 A1 | 2/2013 | Kim et al. |
| 2013/0090652 A1 | 4/2013 | Jenson |
| 2015/0144507 A1 | 5/2015 | Bain |
| 2015/0168336 A1 | 6/2015 | Diguet et al. |
| 2015/0311071 A1 | 10/2015 | Ebata et al. |
| 2016/0103123 A1 | 4/2016 | Holmes et al. |
| 2016/0164010 A1 | 6/2016 | Berger et al. |
| 2016/0169827 A1 | 6/2016 | Hochstetler et al. |
| 2016/0329209 A1 | 11/2016 | Zhuang et al. |
| 2017/0153200 A1 | 6/2017 | Komoto et al. |
| 2017/0184534 A1* | 6/2017 | Goodwin .............. C23C 14/205 |
| 2020/0220168 A1 | 7/2020 | Hochstetler et al. |
| 2020/0271612 A1 | 8/2020 | Hochstetler et al. |
| 2020/0271613 A1 | 8/2020 | Hochstetler et al. |

FOREIGN PATENT DOCUMENTS

| | | |
|---|---|---|
| CN | 101530327 A | 9/2009 |
| CN | 101839884 A | 9/2010 |
| CN | 201697658 U | 1/2011 |
| CN | 102021365 A | 4/2011 |
| CN | 103743805 A | 4/2014 |
| EP | 0176313 A2 | 4/1986 |
| EP | 1347302 A2 | 9/2003 |
| ES | 2186494 A1 | 5/2003 |
| JP | 2001-341227 A | 12/2001 |
| JP | 2003-096577 A | 4/2003 |
| JP | 2003-315302 A | 11/2003 |
| JP | 2004-504604 A | 2/2004 |
| JP | 2004-217977 A | 8/2004 |
| JP | 2014-153280 A | 8/2014 |
| KR | 101303590 B1 | 9/2013 |
| KR | 1397444 B1 | 5/2014 |
| KR | 10-1619109 A | 5/2016 |
| KR | 102013836 | 8/2019 |

(56) References Cited

FOREIGN PATENT DOCUMENTS

| | | |
|---|---|---|
| TW | I244550 B | 12/2005 |
| TW | M286367 | 1/2006 |
| TW | 201504035 A | 2/2017 |
| WO | WO 1996-012315 A | 4/1996 |
| WO | WO 1999-30152 A1 | 6/1999 |
| WO | WO 01-58348 A2 | 8/2001 |
| WO | WO 2010-010211 A2 | 1/2010 |
| WO | WO 2010-122270 A1 | 10/2010 |
| WO | WO 2010-123802 A2 | 10/2010 |
| WO | WO 2016-100266 A1 | 6/2016 |
| WO | WO 2017-112688 A1 | 6/2017 |

OTHER PUBLICATIONS

Co-pending U.S. Appl. No. 14/572,290, filed Dec. 16, 2014, Hochstetler et al.
USPTO Office Action dated Apr. 17, 2015 in co-pending U.S. Appl. No. 14/572,290.
Co-pending U.S. Appl. No. 14/724,563, filed May 28, 2015, Hochstetler et al. Publication No. 2016-0169827, now U.S. Pat. No. 9,506,890.
USPTO Office Action dated Aug. 17, 2015 in co-pending U.S. Appl. No. 14/724,563.
USPTO Office Action dated Mar. 1, 2016 in co-pending U.S. Appl. No. 14/724,563.
Inconell Alloy 600 data sheet, Sep. 2008.
Inconell Alloy 617 data sheet, Mar. 2005.
Notification of Transmittal of the International Search Report and the Written Opinion of the International Searching Authority, or the Declaration dated Mar. 14, 2016 for International Application No. PCT/US2015/065685.
Notification of Transmittal of the International Search Report and the Written Opinion of the International Searching Authority, or the Declaration dated Aug. 14, 2017 for International Application No. PCT/US2017/035353.
Marioli, Juan M. et al., "Electrochemical detection of carbohydrates at nickel-copper and nickel-chromium-iron alloy electrodes", Electroanalysis, vol. 5, No. 1, Jan. 1, 1993, pp. 11-15.
Notification of Transmittal of the International Search Report and the Written Opinion of the International Searching Authority, or the Declaration dated Nov. 8, 2017 for International Application No. PCT/US2017/049312.
Co-pending U.S. Appl. No. 16/332,394, filed Mar. 12, 2019, Hochstetler, et al.
Onoprienko, A., Role of Microstructure in Forming Thin Carbon Film Properties, Diamond Relat. Mater. 1994, 3, pp. 1132-1136.
Onoprienko, A., "Electrical Resistivity and Real Structure of Magnetron-Sputtered Carbon Films", The Future Material for Advanced Technology Applications, Topics Appl. Phys. 100, 2007, pp. 175-186.
Cho, N. H, et atl., Chemical Structure and Physical Properties of Diamond-like Amorphous Carbon Films Prepared by Magnetron Sputtering. J. Mater. Res. 1990, 5, pp. 2543-2554.
ROC (Taiwan) Search Report for Application No. 104142335. Date of Completion Aug. 24, 2019.
Narayan, Roger, "Nanostructured diamondlike carbon thin films for medical applications", Materials Science and Engineering, C, vol. 25, p. 405-416.
Mariolo, et al., "Electrochemical detection of carbohydrates at nickel-copper and nickel-chromium-iron alloy electrodes" Electroanalysis, vol. 5, Isue 1, Jan. 1993, pp. 11-15.
Notice of Allowance and Fee(s) due dated Jul. 25, 2016 received in co-pending U.S. Appl. No. 14/724,563.
Notification of Transmittal of the International Search Report and the Written Opinion of the International Searching Authority, or the Declaration dated Nov. 8, 2017 received in International Application No. PCT/US2017/049281.
Written Opinion of the International Preliminary Examining Authority, dated Aug. 27, 2018 received in International Application No. PCT/US2017/049312.

Notification of Transmittal of the International Search Report and the Written Opinion of the International Searching Authority, or the Declaration dated Aug. 29, 2018 received in International Application No. PCT/US2018/035955.
Co-pending U.S. Appl. No. 16/332,400, filed Mar. 12, 2019; Hochstetler et al., now US Patent Publication No. 2020-0271613.
Co-pending U.S. Appl. No. 16/625,000, filed Dec. 20, 2019; Hochstetler et al., now US Patent Publication No. 2020-0220168.
USPTO Office Action dated Jun. 9, 2021 received in co-pending U.S. Appl. No. 16/332,400.
USPTO Office Action dated Sep. 20, 2021 received in co-pending U.S. Appl. No. 16/332,400.
USPTO Office Action dated Jan. 28, 2022 received in co-pending U.S. Appl. No. 16/332,400.
USPTO Office Action dated May 17, 2022 received in co-pending U.S. Appl. No. 16/332,400.
USPTO Office Action dated Jun. 3, 2022 received in co-pending U.S. Appl. No. 16/625,000.
USPTO Office Action dated Aug. 4, 2022 received in co-pending U.S. Appl. No. 16/332,400.
Ghamousse, et al. Screen-printed carbon electrode modified on its surface with amorphouse carbon nitride thin film: Electrochemical and morphological study, Electrochimica Acta 52, 2007, 5053-5061.
Lee, Sung Pil, "Synthesis and Characterization of Carbon Nitride Films for Micro Humidity Sensors", Sensors, vol. 8, No. 3, Mar. 3, 2008, pp. 1508-1518.
Taiwan Office Action and Search Report, ROC (Taiwan) Patent Application No. 104142335; Date of Completion of Search Aug. 24, 2019.
Taiwan Office Action and Search Report, ROC (Taiwan) Patent Application No. 106130541; Date of Completion of Search Dec. 22, 2020.
Taiwan Office Action and Search Report, ROC (Taiwan) Patent Application No. 107120347; Date of Completion of Search Aug. 13, 2021.
Stanishevsky, Andrei et al., "Quaziamorphous Carbon and Carbon Nitride Films Deposited from the Plasma of Pulsed Cathodic Arc Discharge", Chaos, Solutions and Fractals, vol. 10, No. 12, Jan. 1, 1999, pp. 2045-2066.
Xu et al., "Making co-condensed amorphous carbon/g-C3N4 composites with improved visible-light photocatalytic H2-production performance using Pt as cocatalyst", El Sevier, 2017, Carbon, vol. 118, pp. 241-249.
USPTO Notice of Allowance dated Oct. 19, 2022 in co-pending U.S. Appl. No. 16/332,400.
USPTO Office Action dated Sep. 14, 2022 received in co-pending U.S. Appl. No. 16/625,000.
Notice of Allowance and Fee(s) due dated Nov. 9, 2022 received in co-pending U.S. Appl. No. 16/332,394.
ASTM D 1003-00; Standard Test Methods for Haze and Luminous Transmittance of Transparent Plastics[1].
ASTM F 1711-96 Standard Practice for Measuring Sheet Resistance of Thin Film Conductors for Flat Panel Display Manufacturing Using a Four-Point Probe Method.
Response to the Communication Pursuant to Rules 161(1) and 162 EPC (dated Apr. 25, 2019) filed in the European Patent Office dated Aug. 6, 2019 in Regional Phase EP 17780240.2 based on PCT/US2017/049312.
Response to the Communication Pursuant to Art. 94(3) EPC (dated Mar. 28, 2020) filed in the European Patent Office dated Jul. 2, 2020 in Regional Phase EP 17780240.2 based on PCT/US2017/049312.
Response to the Communication Pursuant to Art. 94(3) EPC (dated Oct. 15, 2020) filed in the European Patent Office dated Apr. 23, 2021 in Regional Phase EP 17780240.2 based on PCT/US2017/049312.
Request for International Preliminary Examination and Response to Written Opinion filed in the European Patent Office dated Mar. 6, 2018 in PCT International Application No. PCT/US2017/049312.
USPTO Office Action dated Jul. 21, 2022 received in co-pending U.S. Appl. No. 16/332,394.
USPTO Office Action dated Jul. 20, 2023 received in co-pending U.S. Appl. No. 16/625,000.

(56) References Cited

OTHER PUBLICATIONS

USPTO Notice of Allowance dated Feb. 15, 2023 in co-pending U.S. Appl. No. 16/332,400.
Notice of Allowance and Fee(s) due dated Mar. 7, 2023 received in co-pending U.S. Appl. No. 16/332,394.
USPTO Office Action dated Mar. 15, 2023 received in co-pending U.S. Appl. No. 16/625,000.

* cited by examiner

PHYSICAL VAPOR DEPOSITED BIOSENSOR COMPONENTS

BACKGROUND

Field of the Invention

The present invention is generally related to electrodes, for example, physical vapor deposited components for electrodes such as those found in biosensors. More particularly, the present invention is related to electrodes formed with non-noble metal alloys, for example, those found in biosensor components.

Description of the Related Art

Biosensors for use in analyzing biological samples are becoming increasingly prevalent. For example, with the rise in cases of diabetes in the world's population, the need for biosensors for measuring blood glucose has risen dramatically. Such biosensors are generally known as glucometers and operate by having a user place a drop of blood on a test-strip associated with the glucometer. The test-strip is configured to be reactive to the amount of glucose in the drop of blood, such that the glucometer can detect and display a glucose level of the user's blood.

The test-strips for glucometer-type biosensors are generally formed with two or more electrodes (e.g., a working electrode and a counter electrode) formed on a substrate. In addition, a bio-reactant that reacts with the biological sample, e.g., an enzyme (e.g., glucose oxidase, glucose dehydrogenase, or the like), and a mediator (e.g., ferricyanide, ruthenium complexes, osmium complexes, quinones, phenothiazines, phenoxazines, or the like) will be formed on one or both electrodes, e.g., the working electrode. In operation of a glucometer-type biosensor, a drop of blood will be applied to a test-strip. Thereafter, an electrochemical reaction proportional to the amount of glucose in the blood will take place on the working electrode. In more detail, glucose first reacts with the bio-reactant, e.g., enzyme (glucose oxidase, glucose dehydrogenase, or the like) and sometimes an enzyme cofactor (PQQ, FAD, or the like) and is oxidized to gluconic acid. The bio-reactant, e.g., enzyme, cofactor, or enzyme-cofactor complex, is temporarily reduced by two electrons transferred from glucose to the enzyme, cofactor, or enzyme-cofactor complex. Next, the reduced bio-reactant, e.g., enzyme, cofactor, or enzyme-cofactor complex, reacts with the mediator, transferring a single electron to each of two mediator species (molecules or complexes), in the case of a mediator that is reduced in a one-electron process. When the mediator species are reduced, the enzyme, cofactor, or enzyme-cofactor complex is thus returned to its original oxidation state. Then, the reduced mediators diffuse to the electrode surface where a pre-determined and sufficiently oxidizing potential is applied to the biosensor so that the reduced mediators are oxidized back to their original oxidation state. The current that is generated by the oxidation of the mediator species by the biosensor is measured and related proportionally to the amount of glucose in the blood.

The quality of the working electrode plays an important role in an accurate measurement of the glucose level of the blood. Specifically, the reproducibility of the electroactive surface area of the electrode, the lot-to-lot repeatability of the electron transfer kinetics of the electrode in a particular glucose measurement arrangement, and long term stability of the electrode material while in storage so that the electrochemical signal that arises from the electrode when the assay is in operation are all factors that lead to improved accuracy of blood glucose test strips. Particularly, it is important that the electrical signals resulting from the electro-activity of the electrode is minimized to prevent bias or noise in the measurement and analysis of biological samples. Typically, this is accomplished by using electrode materials that are intrinsically thermodynamically noble, such as gold, palladium, platinum, iridium, and the like. As such, most current glucometers use electrodes formed from substrates coated with palladium, gold, or other noble metals, generally in the purest form commercially feasible, to function as the working electrode, and for ease of manufacturing, often for the counter electrode or a combined counter and reference electrode. Such noble metals are minimally reactive with interfering substances, and as a result, offer enhanced chemical resistance for consistent and accurate measurements. However, the cost of using such noble metals in electrodes can be prohibitive.

There have been some attempts to use electrodes formed with non-noble metals, so as to reduce manufacturing costs of biosensors. However, such non-noble metal electrodes will generally have an electrochemical response (e.g., dose-responses) that deviates significantly from the electrochemical response of electrodes formed with noble metals. As such, electrodes formed with non-noble metals are generally inadequate for use as direct replacements for noble metals in test-strips for many types of biosensors. In addition to having a low electrical response, it is also desirable for a biosensor electrode to have sufficient electron transfer kinetics with the mediator. While some suggested non-noble metals have a relatively low electrochemical response (or reasonable anodic stability), they do not also have acceptable electron transfer kinetics with a mediator.

Accordingly, there is a need for an electrode which can provide consistent and accurate measurements, while providing a cost effective alternative to the use of noble metals, for example, in biosensors. In particular, there is a need for an electrode formed from a non-noble metal alloy that can be used in a biosensor component to consistently and accurately measure biological samples.

SUMMARY

One or more embodiments of the present disclosure can relate to an electrode which can comprise a substrate and at least one conductive layer coated on the substrate. The conductive layer can comprise nickel and chromium wherein the combined weight percent of the nickel and chromium in the conductive layer can be in the range of 80 to less than 95 weight percent, or 81 to 94 weight percent, or 82 to 94 weight percent, or 83 to 94 weight percent, or 85 to 94 weight percent, or 86 to 94 weight percent, based on the total weight of the conductive layer equaling 100 weight percent. In addition to nickel and chromium, the conductive layer can also comprise iron wherein the weight percent of the iron in the conductive layer can be in the range of greater than 5 weight percent to less than 12 weight percent, or about 6 to about 11 weight percent, or 6 to 11 weight percent, or 6 to 10 weight percent, or 6 to 9 weight percent, or 7 to 10 weight percent, or 7 to 9 weight percent, or about 9 weight percent, based on the total weight of the conductive layer equaling 100 weight percent. While most of this disclosure relates to electrodes used as biosensor components, it is contemplated that the electrodes can be used in other end-use applications as well. As a result, any disclosure herein related to electrodes used in biosensors is intended to incorporate herein applicability to all electrodes that this technology could reasonably be applied to by one of ordinary skill in the art.

One or more embodiments of the present disclosure can relate to a biosensor component which can comprise a substrate and at least one conductive layer coated on the substrate. The conductive layer can comprise nickel and chromium wherein the combined weight percent of the nickel and chromium in the conductive layer can be in the range of 80 to less than 95 weight percent, or 81 to 94 weight percent, or 82 to 94 weight percent, or 83 to 94 weight percent, or 85 to 94 weight percent, or 86 to 94 weight percent, based on the total weight of the conductive layer equaling 100 weight percent.

In one embodiment, the present disclosure relates to a biosensor component comprising a substrate and at least one conductive layer coated on the substrate where the conductive layer can comprise nickel in the range of greater than 70 weight percent and chromium in the range of greater than 13 to less than 20 weight percent and wherein the total combined weight percent of the nickel and chromium in the conductive layer is in the range of greater than 80 to less than 95 weight percent, or 81 to 94 weight percent, or 82 to 94 weight percent, or 83 to 94 weight percent, or 85 to 94 weight percent, or 86 to 94 weight percent, based on the total weight of the conductive layer equaling 100 weight percent.

In one embodiment, the present disclosure relates to a biosensor component comprising a substrate and at least one conductive layer coated on the substrate wherein the conductive layer can comprise nickel in the range of 70 to 81 weight percent, chromium in the range of about 14 to about 19 weight percent, and iron in the range of about 6 to about 11 weight percent and wherein the total combined weight percent of the nickel and chromium in the conductive layer is in the range of about 84 to about 94 weight percent, or 85 to 94 weight percent, or 86 to 94 weight percent, based on the total weight of the conductive layer equaling 100 weight percent.

In one aspect, certain embodiments of the present disclosure relate to a biosensor component comprising a substrate and a conductive layer coated on the substrate wherein the conductive layer can comprise nickel in the range of 70 to 81 weight percent, chromium in the range of 14 to 17 weight percent, and iron in the range of 6 to 11 weight percent, based on the total weight of the conductive layer equaling 100 weight percent.

In one aspect, certain embodiments of the present disclosure relate to a biosensor component comprising a substrate and a conductive layer coated on the substrate wherein the conductive layer can comprise nickel in the range of 72 to 81 weight percent, chromium in the range of 14 to 17 weight percent, and iron in the range of 6 to 11, or 6 to 10, weight percent, based on the total weight of the conductive layer equaling 100 weight percent, and wherein the conductive layer does not include any other element species that is present in an amount greater than 1 weight percent, based on the total weight of the conductive layer equaling 100 weight percent. In one embodiment, the conductive layer further comprises manganese in the range of 0.01 to 1.0 weight percent, and does not include any other element species that is present in an amount greater than 0.5 weight percent, based on the total weight of the conductive layer equaling 100 weight percent.

In one embodiment, the conductive layer can comprise nickel in the range of 72 to 81 weight percent, chromium in the range of 14 to 17 weight percent, and iron in the range of 6 to 11, or 6 to 10, weight percent, based on the total weight of the conductive layer equaling 100 weight percent, and wherein the conductive layer further comprises manganese in the range of 0.01 to 1.0 weight percent, copper in the range of 0.01 to 0.5 weight percent, and silicon in the range of 0.01 to 0.5 weight percent, based on the total weight of the conductive layer equaling 100 weight percent. In an embodiment, the conductive layer contains none or is substantially free of the following element species: molybdenum, niobium, cobalt, aluminum, titanium, phosphorus, or boron, or, if any species is present, such species is in an amount of less than 0.25 weight percent, or less than 0.2 weight percent, or less than 0.1 weight percent, or less than 0.05 weight percent, or trace amounts or less. In an embodiment, the conductive layer contains none, or is substantially free, of the following element species: molybdenum, niobium, cobalt, aluminum, titanium, phosphorus, or boron.

In one aspect, certain embodiments of the present disclosure relate to a biosensor component comprising a substrate and a conductive layer coated on the substrate wherein the conductive layer can comprise nickel in amount greater than 70 weight percent, chromium in the range of greater than 13 to less than 18 weight percent, wherein the combined weight percent of the nickel and chromium in the conductive layer can be in the range of 83 to 94 weight percent, or 84 to 94 weight percent, or 85 to 94 weight percent, or 86 to 94 weight percent, based on the total weight of the conductive layer equaling 100 weight percent. The conductive layer can be coated on a substrate, which can be comprised of at least one of any polymer described in the art and/or described herein including but not limited to polycarbonate, silicone polymers, acrylics, PET, modified PET such as PETG or PCTG, PCT, modified PCT, polyesters comprising TMCD AND CHDM, PCCD, or PEN, by physical vapor deposition.

In certain embodiments of the disclosure, the conductive layer can have a thickness of between 15 and 200 nm, and the substrate can have a thickness of between 25 and 500 μm. In certain embodiments, the biosensor component can also have visible light transmission of no more than 20% or no more than 15% or no more than 10% or no more than 5 or from 0.01 to 20% or from 0.01 to 15% or from 0.01 10% or from 0.01 to 5%, as measured by ASTM D1003.

In certain embodiments, the conductive layer can have a thickness of between 15 and 200 nm, and the substrate can have a thickness of between 25 and 500 μm wherein the biosensor component has a visible light transmission of no more than 20%.

In certain embodiments, the conductive layer can have a thickness of between 15 and 200 nm, and the substrate can have a thickness of between 25 and 500 μm wherein the biosensor component has a visible light transmission of no more than 15%.

In certain embodiments, the conductive layer can have a thickness of between 15 and 200 nm, and the substrate can have a thickness of between 25 and 500 μm wherein the biosensor component has a visible light transmission of no more than 10%.

In certain embodiments, the conductive layer can have a thickness of between 15 and 200 nm, and the substrate can have a thickness of between 25 and 500 μm wherein the biosensor component has a visible light transmission of no more than 5%.

In one aspect, certain embodiments of the present disclosure relate to a biosensor component comprising a substrate and a conductive layer coated on the substrate wherein the conductive layer can comprise nickel in the range of 72 to 81 weight percent, chromium in the range of 14 to 17 weight percent, and iron in the range of 6 to 11 weight percent, based on the total weight of the conductive layer equaling 100 weight percent, and wherein the conductive layer can further comprises manganese in the range of 0.01 to 1.0 weight percent, copper in the range of 0.01 to 0.5 weight percent, and silicon in the range of 0.01 to 0.5 weight percent, based on the total weight of the conductive layer equaling 100 weight percent, and wherein the conductive layer contains none of the following element species: molybdenum, niobium, cobalt, aluminum, titanium, phosphorus, or boron, or, if any species is present, such species is in an amount of less than 0.25 weight percent, or less than 0.2 weight percent, or less than 0.1 weight percent, or less than 0.05 weight percent, or trace amounts or less. The conductive layer is coated on the substrate, which can be comprised of at least one of any polymer described in the art and/or described herein including but not limited to polycarbonate, silicone polymers, acrylics, PET, modified PET such as PETG or PCTG, PCT, PCTA, polyesters comprising TMCD AND CHDM, PCCD, or PEN, by any means known in the art, including but not limited to, physical vapor deposition. The conductive layer has a thickness of between 15 and 200 nm, and the substrate has a thickness of between 25 and 500 μm, such that the biosensor component has a visible light transmission of no more than 20% or no more than 15% or no more than 10% or no more than 5%.

One or more embodiments of the present disclosure can relate to an electrode for a biosensor, with the electrode comprising a substrate and a conductive layer coated on the substrate. The conductive layer can comprise nickel and chromium, and the conductive layer can have an oxidation wave voltage for Fe(II)[CN]$_6$ mediator (identified below as E$_{peak,anodic}$) of less than 400, or less than 375, or less than 350, or less than 325, or less than 300, or less than 275 millivolts (mV), as determined in a Type 1 Linear Sweep Voltammetry Test (as discussed in the Examples section).

In one aspect, embodiments of the present disclosure can relate to an electrode for a biosensor, with the electrode comprising a substrate and a conductive layer coated on the substrate wherein the conductive layer can comprise nickel and chromium, and can have an oxidation wave voltage for Fe(II)[CN]$_6$ mediator (identified below as E$_{peak,anodic}$) of less than 400, or less than 375, or less than 350, or less than 325, or less than 300, or less than 275 millivolts (mV), as determined in a Type 1 Linear Sweep Voltammetry Test (as discussed in the Examples section). In one embodiment, the conductive layer can comprise nickel in amount greater than 70 weight percent, chromium in the range of greater than 13 to less than 18 weight percent, wherein the combined weight percent of the nickel and chromium in the conductive layer can be in the range of 83 to 94 weight percent, or 84 to 94 weight percent, or 85 to 94 weight percent, or 86 to 94 weight percent, based on the total weight of the conductive layer equaling 100 weight percent.

In one aspect, embodiments of the present disclosure can relate to an electrode for a biosensor, with the electrode comprising a substrate and a conductive layer coated on the substrate wherein the conductive layer can comprise nickel and chromium, and can have an oxidation wave voltage for Fe(II)[CN]$_6$ mediator (identified below as E$_{peak,anodic}$) of less than 400, or less than 375, or less than 350, or less than 325, or less than 300, or less than 275 millivolts (mV), as determined in a Type 1 Linear Sweep Voltammetry Test (as discussed in the Examples section). The conductive layer can comprise nickel in the range of 70 to 81 weight percent, chromium in the range of 14 to 17 weight percent, and iron in the of 6 to 11 weight percent, based on the total weight of the conductive layer equaling 100 weight percent.

In one aspect, embodiments of the present disclosure can relate to an electrode for a biosensor, with the electrode comprising a substrate and a conductive layer coated on the substrate wherein the conductive layer can comprise nickel and chromium, and can have an oxidation wave voltage for Fe(II)[CN]$_6$ mediator (identified below as E$_{peak,anodic}$) of less than 400, or less than 375, or less than 350, or less than 325, or less than 300, or less than 275 millivolts (mV), as determined in a Type 1 Linear Sweep Voltammetry Test (as discussed in the Examples section). The conductive layer can comprise nickel in the range of 72 to 81 weight percent, chromium in the range of 14 to 17 weight percent, iron in the range of 6 to 11, or 6 to 10, weight percent, manganese in the range of 0.01 to 1.0 weight percent, copper in the range of 0.01 to 0.5 weight percent, and silicon in the range of 0.01 to 0.5 weight percent, based on the total weight of the conductive layer equaling 100 weight percent. In one embodiment, the conductive layer can have an oxidation wave voltage for Fe(II)[CN]$_6$ mediator (identified below as E$_{peak,anodic}$) of less than 300, or less than 275 millivolts (mV), as determined in a Type 1 Linear Sweep Voltammetry Test (as discussed in the Examples section).

In one aspect, embodiments of the present disclosure can relate to an electrode for a biosensor, with the electrode comprising a substrate and a conductive layer coated on the substrate wherein the conductive layer can comprise nickel and chromium, and can have a an oxidation wave voltage for Fe(II)[CN]$_6$ mediator (identified below as E$_{peak,anodic}$) of less than 400, or less than 375, or less than 350, or less than 325, or less than 300, or less than 275 millivolts (mV), as determined in a Type 1 Linear Sweep Voltammetry Test (as discussed in the Examples section). The conductive layer can comprise nickel in the range of 72 to 81 weight percent, chromium in the range of 14 to 17 weight percent, and iron in the range of 6 to 11, or 6 to 10, weight percent, based on the total weight of the conductive layer equaling 100 weight percent, and wherein the conductive layer further comprises manganese in the range of 0.01 to 1.0 weight percent, copper in the range of 0.01 to 0.5 weight percent, and silicon in the range of 0.01 to 0.5 weight percent, based on the total weight of the conductive layer equaling 100 weight percent. In an embodiment, the conductive layer contains none, or is substantially free, of the following element species: molybdenum, niobium, cobalt, aluminum, titanium, phosphorus, or boron, or, if any species is present, such species is in an amount of less than 0.25 weight percent, or less than 0.2 weight percent, or less than 0.1 weight percent, or less than 0.05 weight percent, or trace amounts or less.

The substrate can be comprised of any polymer composition known in the art including but not limited to at least one polymer selected from the groups consisting of: nylon, polyesters, copolyesters, polyethylene, polypropylene, polyamides; polystyrene, polystyrene copolymers, styrene acrylonitrile copolymers, acrylonitrile butadiene styrene copolymers, poly(methylmethacrylate), acrylic copolymers, poly (ether-imides); polyphenylene oxides or poly(phenylene oxide)/polystyrene blends, polystyrene resins; polyphenylene sulfides; polyphenylene sulfide/sulfones; poly(ester-carbonates); polycarbonates; polysulfones; polysulfone ethers; and poly(ether-ketones); or mixtures of any of the other foregoing polymers.

In one embodiment, the substrate can be comprised of at least one polyester comprising residues of at least one glycol selected from the group consisting of ethylene glycol, 1,4-cyclohexanedimethanol, and 2,2,4,4-tetramethyl-1,3-cyclobutanediol.

In one embodiment, the substrate can be comprised of at least one polyester comprising residues of terephthalic acid and/or dimethyl terephthalate and residues of at least one glycol selected from the group consisting of ethylene glycol, 1,4-cyclohexanedimethanol, and 2,2,4,4-tetramethyl-1,3-cyclobutanediol.

In one embodiment, the substrate can be comprised of at least one polyester comprising an acid component which comprises residues of terephthalic acid and isophthalic acid and/or esters thereof such as dimethyl terephthalate, and at glycol component comprising residues of at least one glycol selected from the group consisting of ethylene glycol residues, 1,4-cyclohexanedimethanol residues, and 2,2,4,4-tetramethyl-1,3-cyclobutanediol.

In one embodiment, the substrate can be comprised of at least one polyester comprising terephthalic acid residues, or an ester thereof, or mixtures thereof, and 1,4-cyclohexanedimethanol residues.

In one embodiment, the substrate can be comprised of at least one polyester made from terephthalic acid residues, or an ester thereof, or mixtures thereof, and 1,4-cyclohexanedimethanol residues and/or 2,2,4,4-tetramethyl-1,3-cyclobutanediol residues.

In one embodiment, the substrate can be comprised of at least one polyester made from terephthalic acid residues, or an ester thereof, or mixtures thereof, 2,2,4,4-tetramethyl-1,3-cyclobutanediol residues, and 1,4-cyclohexanedimethanol residues.

In one embodiment, the substrate can be comprised of at least one polyester made from terephthalic acid residues, or an ester thereof, or mixtures thereof, 2,2,4,4-tetramethyl-1,3-cyclobutanediol residues, and ethylene glycol residues.

In one embodiment, the substrate can be comprised of at least one polyester comprising terephthalic acid residues, or an ester thereof, or mixtures thereof, ethylene glycol residues, and 1,4-cyclohexanedimethanol residues.

Conductive layers in the present disclosure can be constructed of a single layer comprising any of the alloy compositions disclosed in this application. In certain embodiments, the alloy composition contains an alloy which can be a solid solution of the elements (a single phase), a mixture of metallic phases (two or more solutions) or an intermetallic compound with no distinct boundary between the phases.

One or more embodiments of the present disclosure concern a method for forming an electrode for a biosensor. The method comprises (a) providing a substrate; (b) providing a target; and (c) physical vapor depositing at least a portion of said substrate with material from said target to thereby form a conductive layer on said substrate. The conductive material can comprise nickel in the range of greater than 70 weight percent and chromium in the range of greater than 13 to less than 18 weight percent and wherein the total combined weight percent of the nickel and chromium in the conductive layer is in the range of greater than 83 to less than 95 weight percent, or 84 to 94 weight percent, or 85 to 94 weight percent, or 86 to 94 weight percent, based on the total weight of the conductive layer equaling 100 weight percent. Additionally, the conductive layer can have a sheet resistance of less than 2000 ohms per square.

In one aspect, embodiments of the present disclosure can relate to a method for forming an electrode for a biosensor. The method comprises (a) providing a substrate; (b) providing a target; and (c) physical vapor depositing at least a portion of said substrate with material from said target to thereby form a conductive layer on said substrate. The conductive material can comprise nickel and chromium wherein the combined weight percent of the nickel and chromium in the conductive layer can be in the range of 80 to less than 95 weight percent, or 81 to 94 weight percent, or 82 to 94 weight percent, or 83 to 94 weight percent, or 84 to 94 weight percent, or 85 to 94 weight percent, or 86 to 94 weight percent, based on the total weight of the conductive layer equaling 100 weight percent. The conductive layer can have a sheet resistance of less than 2000 ohms per square. In addition to nickel and chromium, the conductive layer can also comprise iron wherein the weight percent of the iron in the conductive layer can be in the range of greater than 5 weight percent to less than 12 weight percent, or about 6 to about 11 weight percent, or 6 to 11 weight percent, or 6 to 10 weight percent, or 6 to 9 weight percent, or 7 to 10 weight percent, or 7 to 9 weight percent, or about 9 weight percent, based on the total weight of the conductive layer equaling 100 weight percent.

In one aspect, embodiments of the present disclosure relate to a method for forming an electrode for a biosensor. The method comprises (a) providing a substrate; (b) providing a target; and (c) physical vapor depositing at least a portion of said substrate with material from said target to thereby form a conductive layer on said substrate. The conductive material can comprise nickel in the range of 72 to 81 weight percent, chromium in the range of about 14 to about 17 weight percent, and iron in the range of about 6 to about 11 weight percent and wherein the total combined weight percent of the nickel and chromium in the conductive layer is in the range of about 84 to about 94 weight percent, or 85 to 94 weight percent, or 86 to 94 weight percent, based on the total weight of the conductive layer equaling 100 weight percent. The conductive layer can have a sheet resistance of less than 2000 ohms per square.

In one aspect, embodiments of the present disclosure relate to a method for forming an electrode for a biosensor. The method comprises (a) providing a substrate; (b) providing a target; and (c) physical vapor depositing at least a portion of said substrate with material from said target to thereby form a conductive layer on said substrate. The conductive material can comprise nickel in the range of 72 to 81 weight percent, chromium in the range of 14 to 17 weight percent, and iron in the range of 6 to 11, or 6 to 10, weight percent, based on the total weight of the conductive layer equaling 100 weight percent.

In one aspect, embodiments of the present disclosure relate to a method for forming an electrode for a biosensor. The method comprises (a) providing a substrate; (b) providing a target; and (c) physical vapor depositing at least a portion of said substrate with material from said target to thereby form a conductive layer on said substrate. The conductive material can comprise nickel in the range of 72 to 81 weight percent, chromium in the range of 14 to 17 weight percent, and iron in the range of 6 to 11, or 6 to 10, weight percent, based on the total weight of the conductive layer equaling 100 weight percent, and wherein the conductive layer can further comprises manganese in the range of 0.01 to 1.0 weight percent, copper in the range of 0.01 to 0.5 weight percent, and silicon in the range of 0.01 to 0.5 weight percent, based on the total weight of the conductive layer equaling 100 weight percent. The conductive layer can have a sheet resistance of less than 2000 ohms per square.

One or more embodiments of the present disclosure concern a method for forming an electrode for a biosensor. The method comprises (a) providing a substrate; (b) providing a target; and (c) physical vapor depositing at least a portion of said substrate with material from said target to thereby form a conductive layer on said substrate. The conductive material can comprise nickel and chromium wherein the combined weight percent of the nickel and chromium in the conductive layer can be in the range of 80 to less than 95 weight percent, or 81 to 94 weight percent, or 82 to 94 weight percent, or 83 to 94 weight percent, or 84 to 94 weight percent, or 85 to 94 weight percent, or 86 to 94 weight percent, based on the total weight of the conductive layer equaling 100 weight percent. The conductive layer can have a sheet resistance, as measured by ASTM F1711-96, of no more than 5000, 2000, 100, 80, 60, 50, 40, 20, 10, or 5 ohms per square. In some embodiments, the conductive layer can have a sheet resistance of between 1 to 5000 ohms per square, 1 to 4000 ohms per square, 1 to 3000 ohms per square, 1 to 2000 ohms per square, 1 to 1000 ohms per square, 1 to 500 ohms per square, 5 to 100 ohms per square, 5 to 20 ohms per square, 5 to 15 ohms per square, 5 to 10 ohms per square, 10 to 80 ohms per square, 20 to 60 ohms per square, or 40 to 50 ohms per square, as measured by ASTM F1711-96. The conductive layer can have a sheet resistance of less than 2000 ohms per square. In addition to nickel and chromium, the conductive layer can also comprise iron wherein the weight percent of the iron in the conductive layer can be in the range of greater than 5 weight percent to less than 12 weight percent, or about 6 to about 11 weight percent, or 6 to 11 weight percent, or 6 to 10 weight percent, or 6 to 9 weight percent, or 7 to 10 weight percent, or 7 to 9 weight percent, or about 9 weight percent, based on the total weight of the conductive layer equaling 100 weight percent. The conductive layer can be coated on the substrate, which can be comprised of any polymer described in the art and/or described herein including but not limited to PET, modified PET such as PETG or PCTG, PCT, modified PCT, polyesters comprising TMCD AND CHDM, PCCD, or PEN, any method known to one of ordinary skill in the art, for example, by physical vapor deposition. The conductive layer can have a thickness of between 15 and 200 nm, and the substrate can have a thickness of between 25 and 500 μm, such that the biosensor component can have a visible light transmission of no more than 20%.

One or more embodiments of the present disclosure concern a method for forming an electrode for a biosensor. The method comprises (a) providing a substrate; (b) providing a target; and (c) physical vapor depositing at least a portion of said substrate with material from said target to thereby form a conductive layer on said substrate. The conductive material can comprise nickel and chromium wherein the combined weight percent of the nickel and chromium in the conductive layer can be in the range of 80 to less than 95 weight percent, or 81 to 94 weight percent, or 82 to 94 weight percent, or 83 to 94 weight percent, or 84 to 94 weight percent, or 85 to 94 weight percent, or 86 to 94 weight percent, based on the total weight of the conductive layer equaling 100 weight percent. The conductive layer can have a sheet resistance of less than 2000 ohms per square. The conductive layer can further comprise nickel in the range of 72 to 81 weight percent, chromium in the range of 14 to 17 weight percent, and iron in the range of 6 to 11 weight percent, based on the total weight of the conductive layer equaling 100 weight percent, and wherein the conductive layer can further comprises manganese in the range of 0.01 to 1.0 weight percent, copper in the range of 0.01 to 0.5 weight percent, and silicon in the range of 0.01 to 0.5 weight percent, based on the total weight of the conductive layer equaling 100 weight percent. The conductive layer is coated on the substrate, which can be comprised of any polymer described in the art and/or described herein including but not limited to PET, modified PET such as PETG or PCTG, PCT, modified PCT, polyesters comprising TMCD AND CHDM, PCCD, or PEN, by any method known to one of ordinary skill in the art, for example, by physical vapor deposition. The conductive layer can have a thickness of between 15 and 200 nm, and the substrate can have a thickness of between 25 and 500 μm, such that the biosensor component can have a visible light transmission of no more than 20%. The electrode can be a working electrode for the biosensor.

One or more embodiments of the present disclosure concern a method for forming an electrode for a biosensor. The method comprises (a) providing a substrate; (b) providing a target; and (c) physical vapor depositing at least a portion of said substrate with material from said target to thereby form a conductive layer on said substrate. The conductive material can comprise nickel and chromium wherein the combined weight percent of the nickel and chromium in the conductive layer can be in the range of 80 to less than 95 weight percent, or 81 to 94 weight percent, or 82 to 94 weight percent, or 83 to 94 weight percent, or 84 to 94 weight percent, or 85 to 94 weight percent, or 86 to 94 weight percent, based on the total weight of the conductive layer equaling 100 weight percent. The conductive layer can have a sheet resistance of less than 2000 ohms per square. The conductive layer can further comprise nickel in the range of 72 to 81 weight percent, chromium in the range of 14 to 17 weight percent, and iron in the range of 6 to 11, or 6 to 10, weight percent, based on the total weight of the conductive layer equaling 100 weight percent, and wherein the conductive layer can further comprises manganese in the range of 0.01 to 1.0 weight percent, copper in the range of 0.01 to 0.5 weight percent, and silicon in the range of 0.01 to 0.5 weight percent, based on the total weight of the conductive layer equaling 100 weight percent. The conductive layer can be coated on the substrate, which can be comprised of any polymer described in the art and/or described herein including but not limited to PET, modified PET such as PETG or PCTG, PCT, modified PCT, polyesters comprising TMCD AND CHDM, PCCD, or PEN, by any method known to one of ordinary skill in the art, for example, by physical vapor deposition. The conductive layer can have a thickness of between 15 and 200 nm, and the substrate can have a thickness of between 25 and 500 μm, such that the biosensor component can have a visible light transmission of no more than 20%. The electrode can be a working electrode for the biosensor, and the biosensor can be a blood glucose sensor.

BRIEF DESCRIPTION OF THE FIGURES

Embodiments of the present disclosure are described herein with reference to the following figures, wherein.

DETAILED DESCRIPTION

Figure 1:
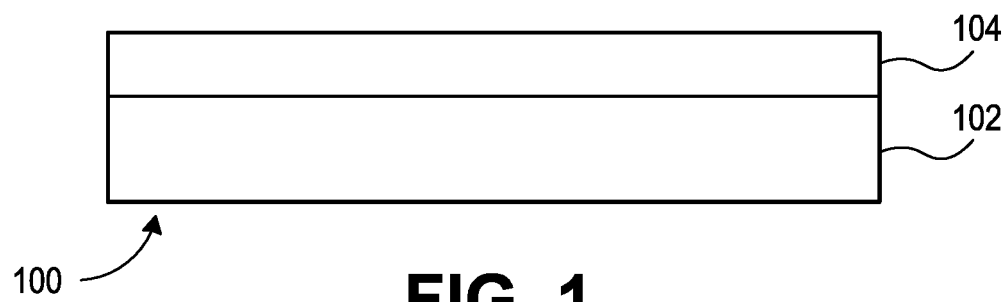
FIG. 1 is a sectional schematic illustration of a thin-film electrode biosensor component of embodiments of the present disclosure.
Figure 2:
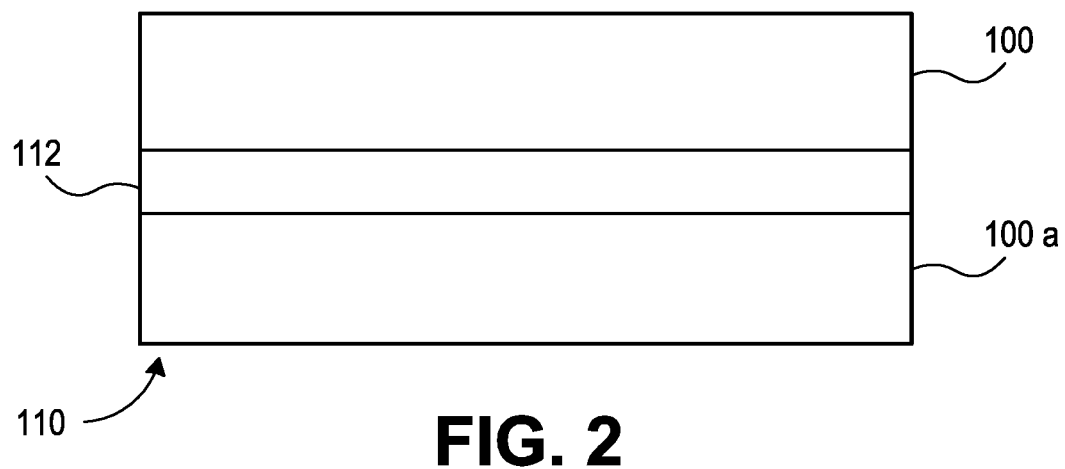
FIG. 2 is a schematic illustration of a test-strip biosensor component of embodiments of the present disclosure.

The present invention is generally directed to a component for an electrode such as those used in a biosensor. As used herein, the term "biosensor" shall denote a device for analyzing biological samples. In some embodiments, as illustrated in FIG. 1, the biosensor component may be a layered thin-film electrode 100 and may broadly comprise a substrate 102 and a conductive layer 104 coated on at least a portion of the substrate 102. In some embodiments, the biosensor may be a medical sensor, such as a glucose measuring system, and the biosensor component may be a test-strip for use with the biosensor. As used herein, the term "medical sensor" shall denote a biosensor used for medical monitoring and/or diagnosis. For instance, as illustrated in FIG. 2, some embodiments contemplate that the biosensor component will comprise a test-strip 110 that includes a first electrode 100 separated from a second electrode 100a by a reaction space 112. The first electrode 100 may comprise a working electrode and the second electrode 100a may comprise a reference electrode or a counter electrode or a combined reference and counter electrode. As such, a biological sample, such as a drop of blood, can be placed within the reaction space 112 and in electrical contact with the first and second electrodes 100 and 100a for analysis. As used herein, the term "blood glucose sensor" shall denote a medical sensor used to determine a concentration of glucose in blood. In addition, a bio-reactant that reacts with the biological sample, e.g., a protein, an enzyme (e.g., glucose oxidase, glucose dehydrogenase, or the like), and a mediator (e.g., ferricyanide, ruthenium complexes, osmium complexes, quinones, phenothiazines, phenoxazines, or the like) can be formed on one or both electrodes, e.g., the working electrode.

Unlike conventional physical vapor deposited biosensor components, which normally include and/or use noble metals such as palladium and/or gold, the biosensor components described herein can be formed from non-noble metals alloys, such as those including nickel and chromium. Nevertheless, the non-noble metals alloys described herein can exhibit superior consistency and accuracy when measuring biological samples. Thus, by using biosensor components comprised of the non-noble metal alloys described herein, the material and manufacturing costs typically associated with the fabrication and use of biosensor components can be significantly reduced.

Embodiments of the present disclosure provide for the substrate 102 to be formed from any type of material, either flexible or rigid, which is generally non-conductive and chemically inert to the contemplated chemical reactions described herein. In certain embodiments, the substrate 102 of the biosensor component may comprise a flexible, non-conductive film, including polymers, such as a polymeric film, a polyester film, a polycarbonate film, or the like. In certain specific embodiments, the substrate 102 may comprise a polyethylene terephthalate (PET) film. Embodiments of the present disclosure contemplate that the substrate 102 may have a thickness of at least 25 µm, 125 µm, or 250 µm, and/or not more than 800 µm, 500 µm, or 400 µm. In certain embodiments, the substrate 102 may have a thickness of between 25 to 800 µm, 25 to 500 µm, or 25 to 400 µm, between 125 to 800 µm, 125 to 500 µm, or 125 to 400 µm, or between 250 to 800 µm, 250 to 500 µm, or 250 to 400 µm.

The conductive layer 104 coated on the substrate 102 may comprise one or more non-noble metals. Such conductive layer 104 may be coated on the substrate 102 via one or more physical vapor deposition techniques, such as sputter coating (e.g., magnetron sputtering, unbalanced magnetron sputtering, facing targets sputtering, or the like), thermal evaporation, electron beam evaporation, arc vaporization, co-evaporation, ion plating, or the like. The conductive layer 104 may be coated on the substrate 102 to a thickness of at least 1, 10, 15, or 30 nm, and/or not more than 1000, 200, 100, or 50, nm. In certain embodiments, the conductive layer 104 may have a thickness of between 1 to 1000 nm, 1 to 200 nm, 1 to 100 nm, or 1 to 50 nm, between 10 to 1000 nm, 10 to 200 nm, 10 to 100 nm, or 10 to 50 nm, between 15 to 1000 nm, 15 to 200 nm, 15 to 100 nm, or 15 to 50 nm, or between 30 to 1000 nm, 30 to 200 nm, 30 to 100 nm, or 30 to 50 nm.

The conductive layer 104 may be coated on the substrate 102, such that the resulting thin-film electrode 100 will generally be opaque to visible light. For example, the resulting thin-film electrode 100 may have a visible light transmission, as measured by ASTM D1003, of no more than 50%, no more than 40%, no more than 30%, or no more than 20%. In certain embodiments, the resulting thin-film electrode 100 may have a visible light transmission of between 1 to 50%, between 10 to 40%, between 15 to 30%, or about 20%. Additionally, the resulting thin-film electrode 100 may have a sheet resistance, as measured by ASTM F1711-96, of no more than 5000, 2000, 100, 80, 60, 50, 40, 20, 10, or 5 ohms per square. In some embodiments, the resulting thin-film electrode 100 may have a sheet resistance of between 1 to 5000 ohms per square, 2 to 2000 ohms per square, 5 to 100 ohms per square, 10 to 80 ohms per square, 20 to 60 ohms per square, or 40 to 50 ohms per square.

Non-noble metals described herein, which form a conductive layer 104, may be comprised of alloys of nickel and chromium. For example, Table 1, below, is illustrative of non-noble metal alloys that were used to prepare conductive layers 104 of a biosensor component. Table 1 includes alloys of nickel and chromium with varying amounts of iron.

In addition to the amounts described above in Table 1, in certain embodiments, the amount of nickel and chromium included in the non-noble metal alloys that comprise the conductive layer of the electrode (for example, conductive layer 104 of the biosensor component) can vary depending on the specific requirements of the electrode, for example, the biosensor component. In various embodiments, the non-noble metal alloys can comprise at least about 70, 71 or 72 and/or up to about 81, 80, 78, 77, 76 or 75 weight percent of nickel. In certain embodiments, the non-noble metal alloys can comprise in the range of about 70 to 81, 71 to 81, 72 to 81, 70 to 80, 70 to 78, 70 to 77, 71 to 80, 71 to 78, 71 to 77, 71 to 75, 72 to 80, 72 to 79, 72 to 78, 72 to 77, 72 to 76, or 72 to 75 weight percent of nickel. Additionally, in various embodiments, the non-noble metal alloys can comprise at least about 12, 13, 14, and/or up to about 25, 20, 19, 18, or 17 weight percent of chromium. More particularly, the non-noble metal alloys can comprise in the range of about 12 to 25, 13 to 20, 13 to 19, 13 to 18, 13 to 17, 14 to 20, 14 to 19, 14 to 18, or 14 to 17 weight percent of chromium.

In certain embodiments, the amount of nickel and chromium included in the non-noble metal alloys that comprise the conductive layer of electrode, for example, the biosensor component, can vary depending on the specific requirements of the biosensor component as follows: 12 to 25 weight % chromium and 70 to 81 weight % nickel; or 13 to 20 weight % chromium and 70 to 81 weight % nickel; or 13 to 19 weight % chromium and 70 to 81 weight % nickel; or 13 to 18 weight % chromium and 70 to 81 weight % nickel; or 13 to 17 weight % chromium and 70 to 81 weight % nickel, or 14 to 20 weight % chromium and 70 to 81 weight % nickel; or 14 to 19 weight % chromium and 70 to 81 weight % nickel; or 14 to 18 weight % chromium and 70 to 81 weight % nickel; or 14 to 17 weight % chromium and 70 to 81 weight % nickel; or 13 to 20 weight % chromium and 71 to 81 weight % nickel; or 13 to 19 weight % chromium and 71 to 81 weight % nickel; or 13 to 18 weight % chromium and 71 to 81 weight % nickel; or 13 to 17 weight % chromium and 71 to 81 weight % nickel; or 14 to 20 weight % chromium and 71 to 81 weight % nickel; or 14 to 19 weight % chromium and 71 to 81 weight % nickel; or 14 to 18 weight % chromium and 71 to 81 weight % nickel; or 14 to 17 weight % chromium and 71 to 81 weight % nickel; or 13 to 20 weight % chromium and 72 to 81 weight % nickel; or 13 to 19 weight % chromium and 72 to 81 weight % nickel; or 13 to 18 weight % chromium and 72 to 81 weight % nickel; or 13 to 17 weight % chromium and 72 to 81 weight % nickel; or 14 to 20 weight % chromium and 72 to 81 weight % nickel; or 14 to 19 weight % chromium and 72 to 81 weight % nickel; or 14 to 18 weight % chromium and 72 to 81 weight % nickel; or 14 to 17 weight % chromium and 72 to 81 weight % nickel; or 13 to 18 weight % chromium and 70 to 80 weight % nickel; or 13 to 17 weight % chromium and 70 to 80 weight % nickel; or 14 to 18 weight % chromium and 70 to 80 weight % nickel; or 14 to 17 weight % chromium and 70 to 80 weight % nickel; or 13 to 18 weight % chromium and 71 to 80 weight % nickel; or 13 to 17 weight % chromium and 71 to 80 weight % nickel; or 14 to 18 weight % chromium and 71 to 80 weight % nickel; or 14 to 17 weight % chromium and 71 to 80 weight % nickel; or 13 to 18 weight % chromium and 72 to 80 weight % nickel; or 13 to 17 weight % chromium and 72 to 80 weight % nickel; or 14 to 18 weight % chromium and 72 to 80 weight % nickel; or 14 to 17 weight % chromium and 72 to 80 weight % nickel; all of these weight percentages being based on the total weight percentages of the conductive layer equaling 100 weight percent.

The non-noble metal alloys that comprise the conductive layer of electrode, for example, the biosensor component, can also include iron. In various embodiments, the non-noble metal alloys can comprise at least about 5, 6, or 7 and/or up to about 12, 11, 10, or 9 weight percent of iron. In certain embodiments, the non-noble metal alloys can comprise in the range of greater than 5 to less than 12, or about 6 to 11, 6 to 10, 6 to 9, 7 to 11, 7 to 10, 7 to 9, or about 9 weight percent of iron, based on the total weight of the conductive layer equaling 100 weight percent.

Non-noble metal alloys other than nickel, chromium and iron that can be present in the invention can include Group I as follows: manganese and copper. Non-noble elements other than nickel, chromium and iron that can be present include Group II as follows: carbon and silicon. Weight percentages of all metal alloys useful in this invention are based on the total weight percentages of materials in the conductive layer equaling 100 weight percent.

In certain embodiments, the conductive layer can further comprise at least about 0.001, 0.01, or 0.1, and/or up to 1.0, 0.9, 0.8, 0.7 or 0.6 weight percent of manganese. In certain embodiments, the non-noble metal alloys can comprise in the range of about 0.001 to 1.0, 0.01 to 1.0, 0.1 to 1.0, or less than about 1.0 weight percent of manganese.

In certain embodiments, the conductive layer can further comprise at least about 0.001, 0.01, 0.1, or 0.2 and/or up to about 0.5, 0.4, or 0.3 weight percent of copper. In certain embodiments, the non-noble metal alloys can comprise in the range of about 0.001 to 0.5, 0.01 to 0.5, 0.1 to 0.5, or less than about 0.5 weight percent of copper.

In certain embodiments, the conductive layer can further comprise a maximum of 0.015 weight percent of silicon. In certain embodiments, the conductive layer can comprise a maximum of 0.15 weight percent of carbon.

In certain embodiments, the conductive layer contains molybdenum, if present, in an amount less than 1, or less than 0.8, or less than 0.6, or less than 0.4, or less than 0.2, or less than 0.1 weight percent, based on the total weight of the conductive layer. In embodiments, the conductive layer is substantially free of molybdenum. In embodiments, the conductive layer contains no molybdenum.

In certain embodiments, the conductive layer contains none or is substantially free of the following element species: molybdenum, niobium, cobalt, aluminum, titanium, phosphorus, or boron, or, in embodiments where any species is present, such species is in an amount of less than 0.25 weight percent, or less than 0.2 weight percent, or less than 0.1 weight percent, or less than 0.05 weight percent, or trace amounts or less. In certain embodiments, the conductive layer contains none or is substantially free of the following element species: molybdenum, niobium, cobalt, aluminum, titanium, phosphorus, or boron.

In certain embodiments, the amount of nickel, chromium and iron included in the non-noble metal alloys that comprise the conductive layer of electrode, for example, the biosensor component, can vary depending on the specific requirements of the biosensor component as follows: 13 to 25 weight % chromium, 70 to 81 weight % nickel and greater than 5 to less than 12 weight % iron; or 13 to 20 weight % chromium, 70 to 81 weight % nickel and 6 to 11 weight % iron; or 13 to 18 weight % chromium, 70 to 81 weight % nickel and 6 to 11 weight % iron; or 14 to 17 weight % chromium, 70 to 81 weight % nickel and 6 to 11 weight % iron; or 13 to 18 weight % chromium, 72 to 81 weight % nickel and 6 to 11 weight % iron, or 14 to 17 weight % chromium, 72 to 81 weight % nickel and 6 to 11 weight % iron; or 14 to 17 weight % chromium, 72 to 81 weight % nickel and 6 to 10 weight % iron, all of these weight percentages being based on the total weight percentages of the conductive layer equaling 100 weight percent.

Conductive layers in the present disclosure can be constructed of a single layer comprising any of the alloy compositions disclosed in this application. In certain embodiments, the alloy composition contains an alloy which can be a solid solution of the elements (a single phase), a mixture of metallic phases (two or more solutions) or an intermetallic compound with no distinct boundary between the phases.

As one skilled in the art would readily appreciate, the elements of the non-noble metal alloys may comprise incidental impurities. As used herein, "incidental impurities" refer to any impurities that naturally occur in the ore used to the produce the non-noble metal alloys or that are inadvertently added during the production process. The non-noble metal alloys can comprise less than about 0.1, 0.05, or 0.001 weight percent of the incidental impurities.

The non-noble metal alloys described herein may also contain one or more additional alloying elements, which are in addition to the elements described above. However, in various embodiments, the non-noble metal alloys can be substantially free from such additional alloying elements. As used herein, the terms "practically free" and "substantially free" mean that the non-noble metal alloy comprises less than 0.001 weight percent of such additional alloying components. Furthermore, the terms "practically free" and "substantially free" may be used interchangeably.

In certain embodiments of the present disclosure, the biosensor components described herein can be prepared by performing the following steps:
(a) providing a substrate;
(b) providing a target; and
(c) physical vapor depositing at least a portion of the substrate with material from the target to thereby form a conductive layer on the substrate.

The providing a substrate of step (a) may include the provision of any type of substrate material, such as PET, as was previously described. In certain embodiments, the substrate will comprise a sheet of substrate material that can be actuated within a high vacuum chamber. The sheet of substrate material may comprise a single section of material, such as a square sheet. In some other embodiments, sheet of substrate material may comprise a roll of material that is passed, via a roll-to-roll mechanism, through the high vacuum chamber, as will be described in more detail below. In other embodiments, the substrate may be held stationary or may be rotated during deposition, as will be also described below.

The providing a target of step (b) may include the provision of a physical vapor deposition target comprised of any of the non-noble metal alloys previously described. For example, in some embodiments, the physical vapor deposition targets comprising the alloys listed in Table 1 (Alloys 1-15) were used to make thin film conductive layers. Such alloy targets may comprise less than about 0.1, 0.05, or 0.001 weight percent of incidental impurities. In some embodiments, the physical vapor deposition target will be housed within and/or will comprise an electrode, such as a sputter cathode, during the physical vapor deposition process. In certain embodiments, the physical vapor deposition target may be a circular, having a diameter of at least 2, 4, 8, 12, 16, or 20 cm. In other embodiments, the physical vapor deposition target may be a tubular target having an inner diameter of at least 2, 4, 8, or 16 cm and an outer diameter of 20, 24, 28 or 32 cm. In still other embodiments, the physical vapor deposition target may be rectangular with dimensions of: a width of between 5 to 25 cm, a length of between 25 to 75 cm, and a thickness of between 0.3 to 5 cm. It should be understood, however, that embodiments of the present disclosure contemplate the use of other-shaped and sized targets.

The physical vapor depositing of step (c) generally includes the coating of the substrate with the material from the non-noble metal alloy target to form the conductive layer. As used herein, the term "physical vapor deposition" shall denote depositing thin-films by providing for the condensation of vaporized material onto a substrate. The physical vapor deposited coating may be performed with any type of physical vapor deposition process previously described, i.e., sputter coating, thermal evaporation, electron beam evaporation, arc vaporization, co-evaporation, ion plating, or the like. For example, in some embodiments, the physical vapor depositing step will be performed via a sputtering process, in which the substrate is coated with the conductive layer by sputtering the non-noble metal alloy target via the sputtering device. Specific examples of such a sputtering-type physical vapor depositing will be described in more detail below. The resulting substrate with the conductive layer coated thereon may be used as a biosensor component, such as an electrode. Such electrodes may include a working electrode, a reference electrode, and/or a counter electrode. In certain embodiments, such as when a roll of substrate material is vacuum coated with a conductive layer, via a roll-to-roll physical vapor deposition process, the resulting thin-film sheet may be cut apart to appropriate size to form a thin-film electrode specifically sized for the biosensor component. In other embodiments, the biosensor components can be formed from the thin-film sheet by etching, such as chemical or laser etching. In still other embodiments, the biosensor components can be formed using a patterned mask, which is laid on the substrate, and the conductive layer is physical vapor deposited thereover to form the biosensor component.

In certain specific embodiments, the biosensor components may be created via a roll-to-roll physical vapor deposition process that includes roll-to-roll magnetron sputtering. For instance, a substrate sheet comprising a polymer film made of PET (polyethyleneptrapthalate) with a thickness ranging from 25 μm to 250 μm and width of 33.02 cm may be sputtered using a 77.50 cm wide web roll-to-roll magnetron sputter coater, such as a the Smartweb coater offered by Applied Materials, Inc. or the Mark 80 offered by CHA Industries, Inc. A single or a dual target configuration can be employed to deposit a conductive layer of non-noble metal alloys, such as those alloys from Table 1. A target comprised of a non-noble metal alloy plate (such as is available from Tricor Industries Inc.) can be used. A vacuum chamber of the sputter coater can be pumped down to base pressure of at least $10^{-5}$ Torr using a diffusion and mechanical pump combination. In other embodiments a combination of a mechanical pump, a turbo pump, a cryo pump, and/or an oil diffusion pump may be used. Magnetron sputtering cathodes housing the non-noble metal alloy targets having a generally rectangular shape of 15.24 cm×30.48 cm can be energized using 2 KW power supplies (such as offered from Advanced Energy Inc.). An argon gas flow into the vacuum chamber can be controlled (such as via a MKS model 1179A flow controller) to set a sputtering pressure between 3 to 10 mTorr for use during the sputtering process.

A thickness and sheet resistance of the sputtered conductive layer can be efficiently controlled in-situ by controlling specific process parameters. Examples of process parameters include roll-to-roll web speeds (i.e., controlling the speed of the substrate sheet as it travels through the vacuum chamber during sputtering), power supplied to the sputtering targets (i.e. a product of the applied voltage and current to the plasma formed near the target surface), gas pressure in the sputtering chamber, and the number of targets present in the chamber. For example, for sputtering of a conductive layer of a given alloy, the web speed can be set to between 0.1 to 3.5 meters per minute and sputtering power density of between 2 to 8 Watts per square cm. As such, sputtered conductive layer of the alloy may be formed having a measured thickness value of about 25 nm and a sheet resistance of about 45 ohms per square.

In addition to the roll-to-roll process described above, biosensor components can be manufacture using a scaled-up version of the same geometry, using a large-scale roll-to-roll process. In such a large-scale roll-to-roll process, maximum web speeds can be 0.1 to 10 meters per minute, between 3 to 7 meters per minute, or higher than 10 meters per minute. The large-scale roll-to-roll process may provide a sputtering power density between 0.1 to 13, 2 to 10, or 5 to 8 Watts per square cm. Additionally, the number of targets can include between 2, 4, 6 or more, and the web width of the substrate sheet can be from 75 cm or larger.

Embodiments additionally contemplate that physical vapor deposition processes can be utilized in which substrate sheets are held stationary within the vacuum chamber. Certain of such embodiments, are described in detail below in the Examples section. In some embodiments in which the substrate sheets are held stationary, deposition times for depositing the conductive layer on the substrate sheets may be 5, 10, 15, 30 minutes or more.

As previously noted above, biosensor components that include conductive layer formed from the non-noble metal alloys described herein can exhibit desirable electrochemical properties that make them particularly well suited as replacements for biosensor components that incorporate noble metals, such as palladium and/or gold. For instance, the biosensor components of embodiments of the present disclosure may comprise a thin-film electrode formed with a non-noble metal alloy conductive layer that exhibits desirable dose-response characteristics when undergoing chronoamperometry tests.

In various embodiments, the conductive layer can comprise nickel, chromium, and iron (in amounts as discussed above) and the conductive layer can have an oxidation wave voltage for Fe(II)[CN]$_6$ mediator (identified below as $E_{peak, anodic}$) of less than 400, or less than 390, or less than 380, or less than 375, or less than 360, or less than 350, or less than 340, or less than 330, or less than 325, or less than 320, or less than 310, or less than 300, or less than 290, or less than 280, or less than 275, or less than 270, or less than 260 millivolts (mV), as determined in a Type 1 Linear Sweep Voltammetry Test (as discussed in the Examples section).

This invention can be further illustrated by the following examples of embodiments thereof, although it will be understood that these examples are included merely for the purposes of illustration and are not intended to limit the scope of the invention unless otherwise specifically indicated.

Examples

Preparation of Thin-Film Electrodes

For each of the below-described examples, biosensor components in the form of thin-film electrodes were formed by the following-described physical vapor deposition process. It is understood that thin-film electrodes can be formed, using the below process, to include a conductive layer of a plurality of different types of elements and element alloys, such as the non-noble compositions listed in Table 1, as well as noble metals, such as palladium and gold. The process included forming thin-film electrode films by:

(a) metal or metal alloys were deposited on 10.16 cm×10.16 cm square PET substrate sheet using direct current ("DC") magnetron sputtering in a high vacuum chamber, with the sputtering having been performed with a Denton Vacuum Desktop Pro sputtering device;

(b) the vacuum chamber was evacuated to an initial base pressure of ~10$^{-5}$ Torr;

(c) argon gas of 10 sccm was introduced into the high vacuum chamber to create a deposition pressure of 4 mTorr;

(d) the substrate sheets were rotated at approximately two revolutions per minute within the vacuum chamber;

(e) a 5.08 cm diameter target of the metal or metal alloys was held at a constant power of 40 Watts under the DC magnetron sputtering device for deposition time of 15 minutes to coat at least a portion of the substrate sheet with the conductive layer (to initialize the targets, the targets were held at a constant power of 40 Watts under the DC magnetron sputtering device for a 5 minute pre-sputtering time prior to the substrates being introduced into the vacuum chamber); and (f) all depositions were carried out at room temperature.

Individual thin-film electrodes, with a size of 5.08 cm×7.62 cm, were cut from the thin-film electrode films that were formed by physical vapor deposition, as provided above. Electrochemical experiments were conducted using a Gamry Instruments Reference 600 potentiostat in a three electrode configuration, with the electrochemical cell containing the thin-film electrode film positioned inside of a Gamry Instruments VistaShield Faraday Cage. Each of the thin-film electrodes was formed as a working electrode by partially masking the thin-film electrode with electroplating tape having a single 3 mm diameter aperture die-cut into it. As such, an unmasked portion formed by the die-cut aperture of the thin-film electrode provided a geometric working electrode surface area of 0.0707 square cm. Another different area of unmasked portion of the thin-film electrode served as an electrical connection point to a working electrode lead of the potentiostat. The masked portion of the thin-film electrode was placed onto a flat supporting block of non-conductive material, such as plastic. The thin-film electrode was thereafter placed into a working electrode port of a glass electrochemical cell. The exposed 3 mm diameter portion of the thin-film electrode was positioned near a center of a bottom opening of working electrode port of the electrochemical cell. The working electrode port of the electrochemical cell was sealed with a clamp and an O-ring. The electrochemical cell also contained a reference electrode comprising a saturated calomel reference electrode and a carbon auxiliary electrode. The reference electrode and the auxiliary electrode were placed, respectively in a reference electrode port and an auxiliary electrode port. Additionally, the reference electrode and the auxiliary electrode were connected, respectively, to a reference lead and an auxiliary lead of the potentiostat. The electrochemical cell also included a gas flow port by which to deaerate and blanket test solutions with inert gas, such as nitrogen.

Thin film electrodes were prepared from alloys containing varying amounts of nickel, chromium and iron according to the procedures discussed above. The alloys used are listed below in Table 1.

TABLE 1

| Alloys (Elements in wt %) | | | | | |
|---|---|---|---|---|---|
| Alloy | Ni | Cr | Fe | $E_{peak, anodic}$ (V vs SCE) | $i_{0.76 V}$ (microamps) |
| 1 | 79 | 20 | 1 | 0.24 | 98.6 |
| 2 | 78 | 20 | 2 | 0.24 | 95.5 |
| 3 | 77 | 20 | 3 | 0.24 | 78.9 |
| 4 | 76 | 20 | 4 | 0.24 | 60.2 |
| 5 | 75 | 20 | 5 | 0.25 | 49.7 |
| 6 | 75 | 19 | 6 | 0.26 | 40.5 |
| 7 | 75 | 18 | 7 | 0.26 | 30.8 |
| 8 | 75 | 17 | 8 | 0.26 | 22.7 |
| 9 | 75 | 16 | 9 | 0.26 | 17.6 |
| 10 | 75 | 16 | 9 | 0.3 | 21.2 |
| 11 | 68 | 20 | 12 | >0.35 (broad) | 17.6 |
| 12 | 75 | 13 | 12 | >0.35 (broad) | 19.1 |
| 13 | 65 | 20 | 15 | >0.35 (broad) | 13.2 |
| 14 | 60 | 20 | 20 | 0.4 | 10.2 |
| 15 | 50 | 20 | 30 | >0.35 (broad) | 9.2 |

Alloys 1-8 and 10-15 were custom made with the composition according to Table 1. These alloys are believed to be substantially free of any other elements. Alloy 9 was a commercially available INCONEL® 600 Alloy, which is believed to include additional trace (or higher) concentrations of certain elements not shown in Table 1.

Additional thin film electrodes were prepared from commercially available non-noble metal alloys. The commercial alloys used were all sold under the trade name Inconel®. The reported alloy compositions for the various Inconel® metal alloys are listed in Table 2 below.

addition, thin-film electrodes formed with a conductive layer of various INCONEL® metal alloys listed in Table 2 were tested.

The results of such tests are illustrated graphically in FIGS. 3-7. Table 1 shows a numerical representation of oxidation wave voltage of $Fe(II)[CN]_6$ mediator (data is listed in column titled $E_{peak,anodic}$). Table 1 also shows the

TABLE 2

Inconel ® Alloys (source: www.specialmetals.com/alloys)

Element (% by mass)

| Inconel | Ni (min) | Cr | Fe | Mo | Nb | Co | Mn | Cu | Al | Ti | Si | C | S | P |
|---|---|---|---|---|---|---|---|---|---|---|---|---|---|---|
| 600 | 72 | 14-17 | 6-10 | | | | 1* | 0.5* | | | 0.5* | 0.15* | 0.015* | |
| 625 | 58 | 20-23 | 5* | 8-10 | 3.15-4.15 | 1* | 0.5* | | 0.4* | 0.4* | 0.5* | 0.1* | 0.015* | 0.015* |
| X750 | 70 | 14-17 | 5-9 | | 0.7-1.2 | 1* | 1* | 0.5* | 0.4-1 | 2.25-2.75 | 0.5* | 0.08* | 0.01* | |

*denotes maximum concentration

Type 1 Linear Sweep Voltammetry Test Description

A Type 1 Linear Sweep Voltammetry Test can be used to test the electrochemical response of the thin-film electrodes. The Type 1 Linear Sweep Voltammetry Test comprises the following steps: 50 mL of 10 mM potassium phosphate buffer containing 145 mM sodium chloride at pH 7.1 was placed into the electrochemical cell and the electrochemical cell was sealed with stoppers. Gas inlet and outlet fittings, which were associated with the gas flow port, allowed inert gas sparging (i.e., de-aerating) of the buffer solution, via a gas flow of nitrogen, using a medium-porous filter stick. The gas flow port additionally allowed the gas flow to be switched from the filter stick to a headspace-blanketing arrangement. The gas outlet was connected to an oil bubbler to prevent back-diffusion of external gas (e.g., air) into the electrochemical cell. The buffer solution was stirred with a magnetic stirbar while simultaneously sparged with nitrogen for at least 5 minutes before switching the gas flow to a blanketing configuration. No agitation of the buffer solution from sparging or otherwise was otherwise present during the electrochemical experiments conducted via the Type 1 Linear Sweep Voltammetry Test (i.e., the solution was quiescent during electrochemical testing).

A linear sweep voltammetry test was performed on the thin-film electrode that comprised the working electrode within the electrochemical cell. The initial voltage potential for linear sweep voltammetry was 0 V versus the open circuit potential (also known as the rest potential), as measured between the working electrode and the reference electrode (i.e., the saturated calomel reference electrode), and after a rest period of at least 10 seconds prior to the voltammetric experiment, the voltage potential was swept anodically at 25 mV per second until a current of at least 50 µA was observed. For solutions that contained $Fe(II)[CN]_6$ mediator, the mediator was present at 1 mM concentration and the linear sweep voltammetry conditions were otherwise identical to mediator-free solutions.

Application of Type 1 Linear Sweep Voltammetry Test to Thin-Film Electrodes

Figure 3:
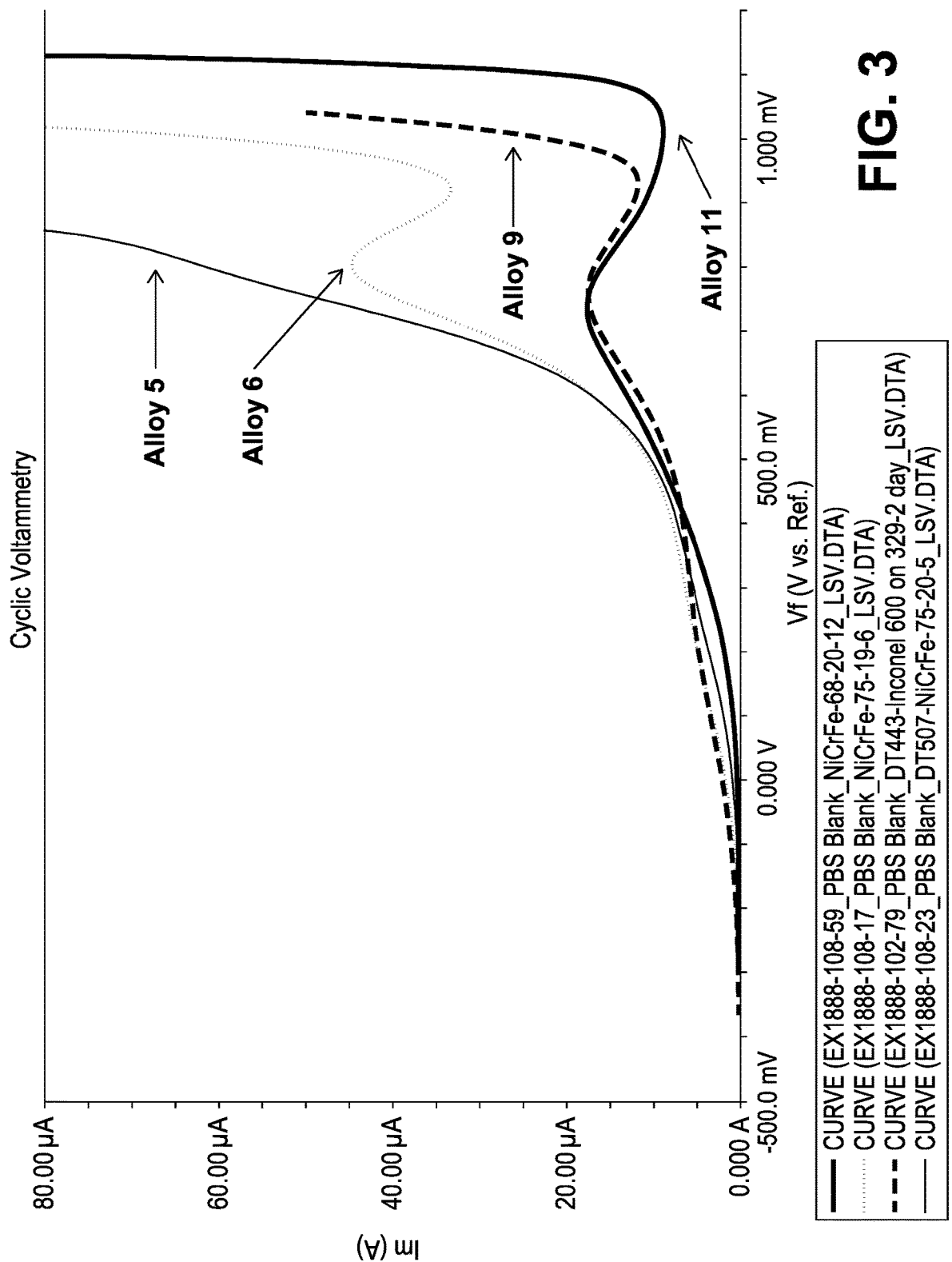
FIG. 3 is a graph depicting a linear sweep voltammogram plot of thin-film electrodes in a mediator-free solution.
Figure 5:
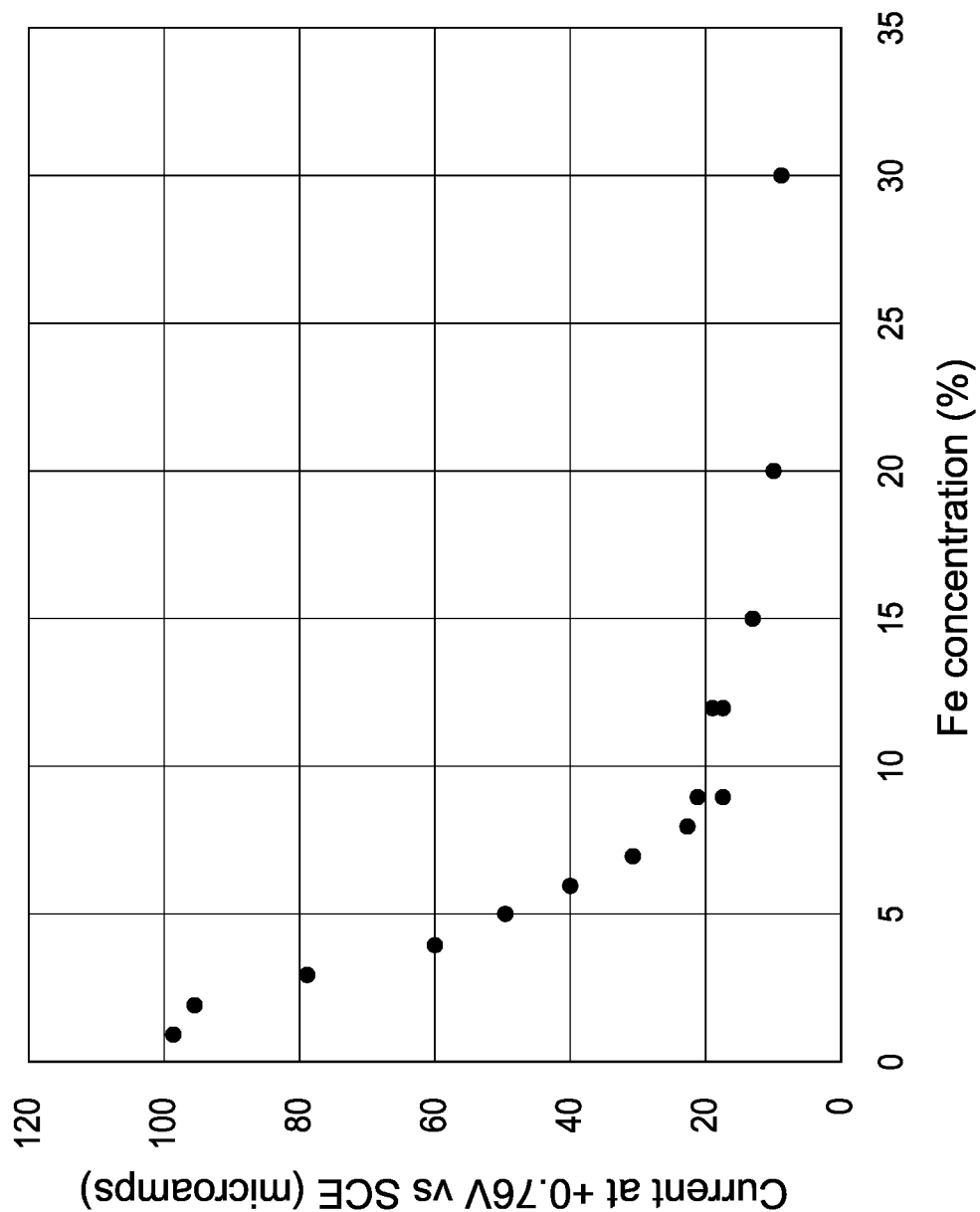
FIG. 5 is a graph depicting the measured current in microamps at a voltage of +0.76V vs an SCE reference electrode in a mediator-free solution as a function of iron concentration in a series of thin film electrodes.

A plurality of different thin-film electrodes were tested using the Type 1 Linear Sweep Voltammetry Test. In more detail, a thin-film electrode formed with a conductive layer selected from each of the non-noble metal alloys listed in Table 1 (Alloys 1-15) was tested. Specifically, the following thin-film electrodes were tested: thin-film electrodes formed with a conductive layer of Alloys 1-15, respectively. In addition, thin-film electrodes formed with a conductive layer of various INCONEL® metal alloys listed in Table 2 were tested.

peak anodic current of the oxidation wave that occurs at +0.76V vs the SCE reference electrode (data is listed in column titled $i_{0.76V}$). This peak anodic current value may be interpreted as an indicator of anodic stability of any particular alloy listed in Table 1. It can be generally desirable for the thin-film electrodes used in biosensors to exhibit a peak anodic current for $Fe(II)[CN]_6$ that occurs at a voltage as low as possible. It can also generally be desirable for the thin-film electrodes used in biosensors to exhibit minimized and/or reduced currents under the influence of certain electrode potentials. FIG. 3 is a plot of a Type 1 linear sweep voltammetry test conducted on certain alloys from Table 1 using a mediator-free phosphate buffer solution and illustrates the background current or anodic stability of the alloys as a function of iron content. As illustrated in FIG. 3, the thin-film electrodes formed from Alloys 5, 6, 9, and 11 (from Table 1) show that anodic breakdown continues to improve as the iron content increases. As illustrated in FIG. 5, the current at +0.76V vs SCE decreases rapidly at low Fe concentrations in the alloys and then more slowly in the 8-30% Fe concentration range. A review of FIG. 3 reveals that increasing iron content of the alloys tested from 5 to 12 wt % leads to greater anodic stability. It can generally be a desirable characteristic of an electrode film to have sufficient anodic stability so that oxidation of the electrode itself is not a significant contributor to the current measured by the glucose meter, which (oxidation of the electrode) would lead to positive bias and lessened accuracy of the reported glucose result.

Figure 4:
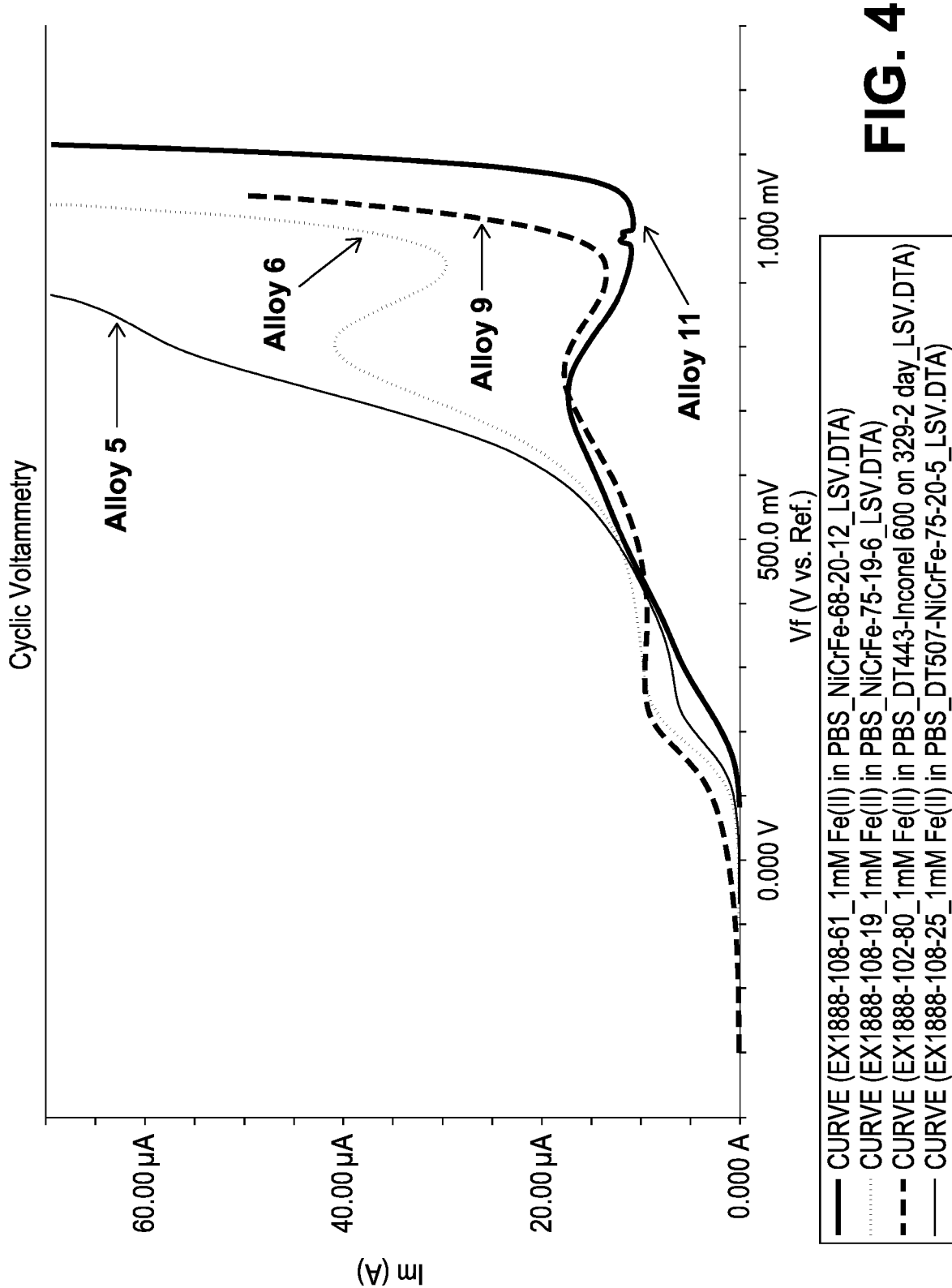
FIG. 4 is a graph depicting a linear sweep voltammogram plot of thin-film electrodes in a mediator-containing solution.
Figure 6:
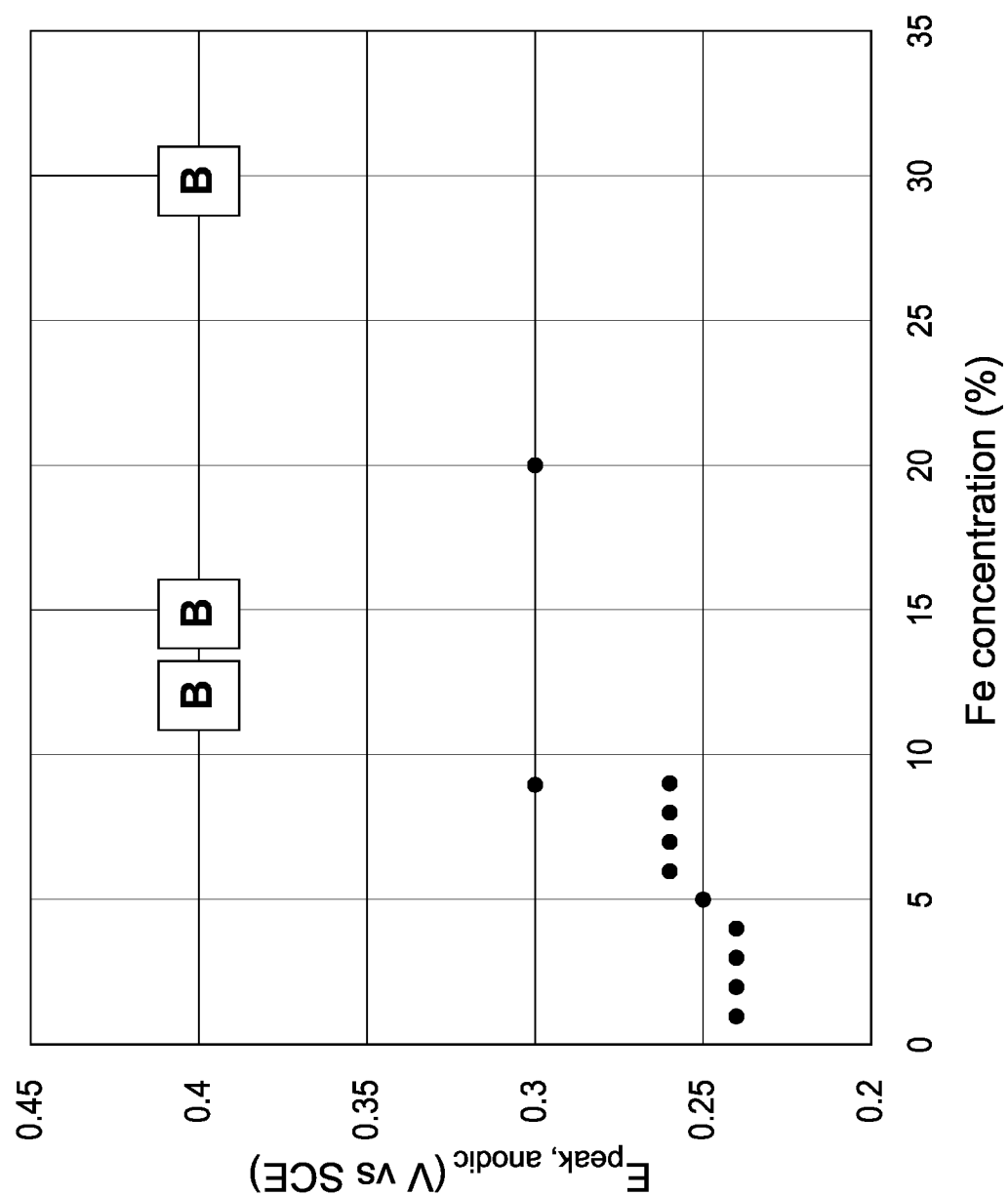
FIG. 6 is a graph depicting the voltage at which the peak current for the oxidation of Fe(II)[CN]$_6$ mediator occurs.

FIG. 4 is a plot of a Type 1 linear sweep voltammetry test conducted on the same alloys from Table 1 that were used for FIG. 3 (Alloys 5, 6, 9 and 11) using a phosphate buffer solution and a $Fe(II)[CN]_6$ mediator, and illustrates the heterogeneous electron transfer kinetics with the $Fe(II)[CN]_6$ mediator for these alloys as indicated by the voltage at which oxidation of $Fe(II)[CN]_6$ occurs. FIG. 6 illustrates the voltage for the oxidation wave for all alloys listed in Table 1. For certain alloys, heterogeneous electron transfer kinetics were so slow that it was difficult to distinguish a wave for the oxidation of $Fe(II)[CN]_6$ mediator. For these difficult to distinguish waves, the letter "B" is plotted at +0.4V which indicates that the waves were broad and difficult to identify as a discrete oxidation wave. A higher positive (more anodic) voltage indicates slower heterogeneous electron transfer kinetics. Generally, it may be desirable for an electrode material in a sensor such as a blood glucose sensor to have as fast as possible heterogenous electron transfer kinetics so that the applied oxidizing voltage that is required to operate the sensor is as small as possible. In some embodiments, a biosensor may be operated at a voltage sufficiently anodic to cause the working electrode current to be controlled by the diffusion of electroactive species (e.g., mediator). If the applied voltage is too oxidizing, oxidation of interferent species that might be present in blood, such as uric acid, acetaminophen, and the like, might be oxidized. This could result in undesired positive bias in the determined glucose concentration and a less accurate sensor. There is, therefore, a need to have both sufficiently fast heterogeneous electron transfer kinetics to enable as mild (e.g., low) oxidation potentials as possible and a sufficiently anodically stable electrode film material to prevent large background oxidation currents arising from the oxidation of the electrode material itself. A review of FIG. 4 reveals that heterogeneous electron transfer kinetics with ferrocyanide significantly increases for the alloy containing 8 wt % iron compared to the alloy containing 12 wt % iron. Higher iron content continues to slow electron transfer kinetics to a point where it becomes no longer useful in a biosensor application. It is believed that an electrode film used in a biosensor should have an adequate balance between sufficiently fast heterogeneous electron transfer kinetics and sufficient anodic stability to be useful.

Figure 7:
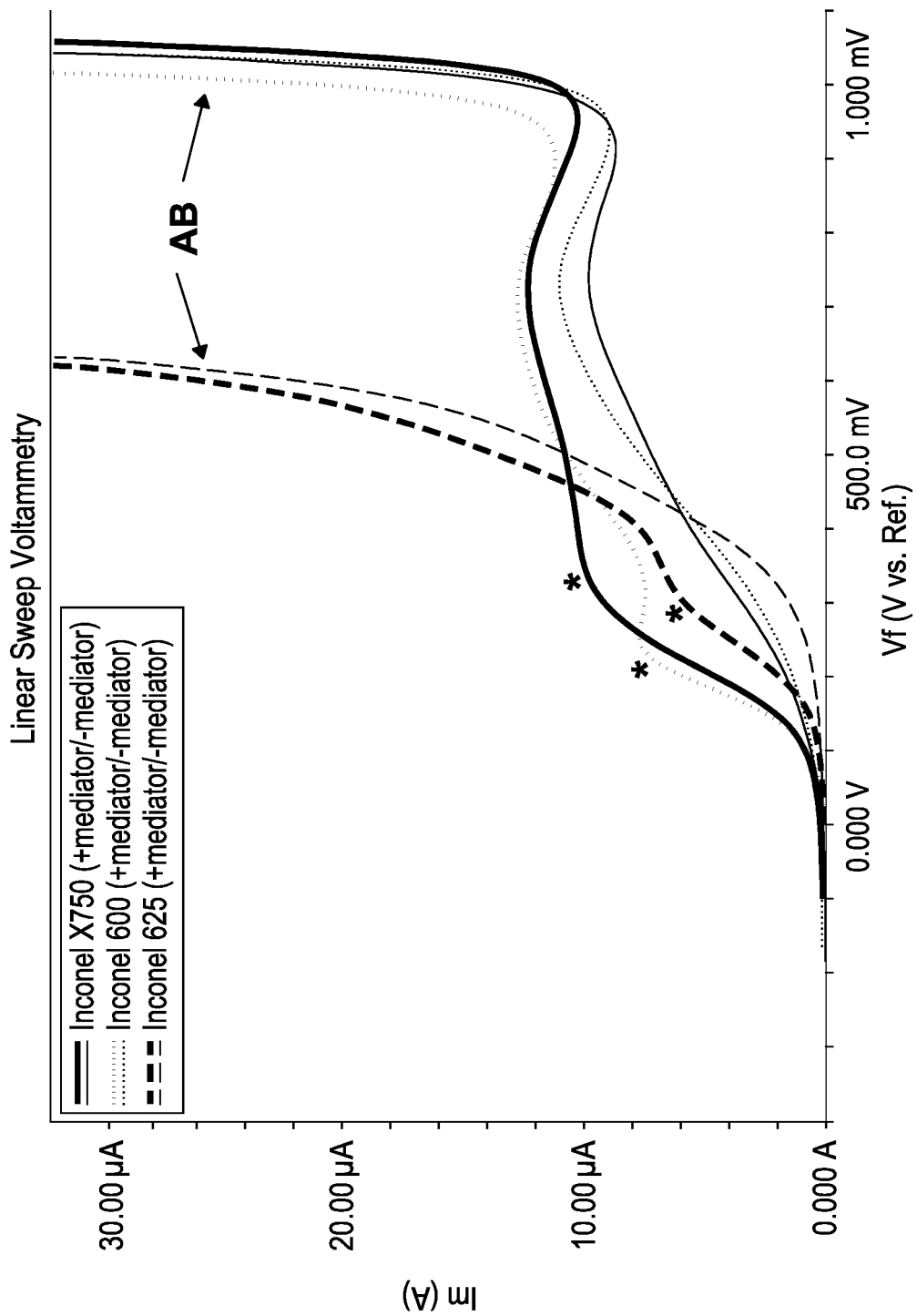
FIG. 7 is a graph depicting a linear sweep voltammogram plot of certain Inconel® alloys listed in Table 2 in both mediator-free and Fe(II)[CN]$_6$ mediator-containing buffer solutions.

FIG. 7 is a plot of a Type 1 linear sweep voltammetry test conducted on alloys from Table 2 using a phosphate buffer solution and a $Fe(II)[CN]_6$ mediator and illustrates the heterogeneous electron transfer kinetics with the ferrocyanide for these alloys. $Fe(II)[CN]_6$ oxidation waves for each of the three alloys are indicated with a * in the plot. A review of FIG. 7 reveals that the Inconel® 600 alloy has superior electron transfer kinetics to both Inconel® 625 and Inconel® X750 alloys, as indicated by a less anodic oxidation wave. Further review of FIG. 7 reveals that the anodic stability of Inconel 625 is significantly less than that of Inconel® 600 and Inconel® X750 as indicated by the potentials at which oxidation current resulting from the anodic breakdown of the electrode film rapidly rises (labeled with "AB" in the plot). Inconel® 783 alloy was too magnetic to sputter (through DC magnetron sputtering) and a thin film electrode could not be formed.

The above detailed description of embodiments of the disclosure is intended to describe various aspects of the invention in sufficient detail to enable those skilled in the art to practice the invention. Other embodiments can be utilized and changes can be made without departing from the scope of the invention. The above detailed description is, therefore, not to be taken in a limiting sense. The scope of the present invention is defined only by claims presented in subsequent regular utility applications, along with the full scope of equivalents to which such claims are entitled.

In this description, references to "one embodiment," "an embodiment," or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, step, etc. described in one embodiment may also be included in other embodiments, but is not necessarily included. Thus, the present technology can include a variety of combinations and/or integrations of the embodiments described herein.

The inventors hereby state their intent to rely on the Doctrine of Equivalents to determine and assess the reasonably fair scope of the present disclosure as it pertains to any apparatus not materially departing from but outside the literal scope of the invention as set forth in the following claims.

Definitions

It should be understood that the following is not intended to be an exclusive list of defined terms. Other definitions may be provided in the foregoing description, such as, for example, when accompanying the use of a defined term in context.

As used herein, the terms "a," "an," and "the" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," and "have" have the same open-ended meaning as "comprising," "comprises," and "comprise" provided above.

As used herein, the terms "including," "include," and "included" have the same open-ended meaning as "comprising," "comprises," and "comprise" provided above.'

Numerical Ranges

The present description uses numerical ranges to quantify certain parameters relating to the invention. It should be understood that when numerical ranges are provided, such ranges are to be construed as providing literal support for claim limitations that only recite the lower value of the range as well as claim limitations that only recite the upper value of the range. For example, a disclosed numerical range of 10 to 100 provides literal support for a claim reciting "greater than 10" (with no upper bounds) and a claim reciting "less than 100" (with no lower bounds).

What is claimed is:

1. A biosensor component for use in analyzing a biological sample, said biosensor component comprising:
   a substrate;
   a conductive layer coated on said substrate, and
   a biological reactant for electrochemically reacting with said biological sample,
   wherein said conductive layer comprises nickel, chromium and iron,
   wherein a combined weight percent of the nickel and chromium in the conductive layer is in the range of 80 to less than 95 weight percent,
   wherein the weight percent of iron in the conductive layer is greater than 5 weight percent and less than 12 weight percent.

2. The biosensor component according to claim 1, wherein said biosensor component comprises an electrode.

3. The biosensor component according to claim 2, wherein said electrode is a working electrode or a reference electrode or a counter electrode.

4. The biosensor component according to claim 1, wherein the biosensor is a blood glucose sensor.

5. The biosensor component according to claim 1, wherein said biosensor component comprises a test-strip.

6. The biosensor component according to claim 1, wherein said substrate has a thickness between 25 and 500 µm and said conductive layer has a thickness between 15 and 200 nm.

7. The biosensor component according to claim 1, wherein said conductive layer is physical vapor deposited on said substrate.

8. The biosensor component according to claim 7, wherein said conductive layer is sputtered on said substrate.

9. The biosensor component according to claim 1, wherein the weight percent of iron in the conductive layer is in the range from about 6 to about 11 weight percent.

10. The biosensor component according to claim 9, wherein the weight percent of nickel in the conductive layer is at least 70 weight percent.

11. The biosensor component according to claim 10, wherein the weight percent of chromium in the conductive layer is greater than 13 weight percent and less than 18 weight percent.

12. The biosensor component according to claim 11, wherein the weight percent of chromium in the conductive layer is in the range from about 14 to about 17 weight percent.

13. The biosensor component according to claim 12, wherein the weight percent of nickel in the conductive layer is about 72 weight percent or greater.

14. The biosensor component according to claim 1, wherein the conductive layer does not include any other element species that is present in an amount greater than 1 weight percent, based on the total weight of the conductive layer equaling 100 weight percent.

15. The biosensor component according to claim 1, wherein the conductive layer comprises 0 to 0.2 weight percent molybdenum.

16. The biosensor component according to claim 15, wherein the conductive layer contains no molybdenum.

17. The biosensor component according to claim 1, wherein said substrate comprises a flexible, non-conductive film.

18. The biosensor component according to claim 1, wherein said substrate comprise polyethylene terephthalate (PET).

19. The biosensor component according to claim 1, wherein said biosensor component has a visible light transmission of no more than 20%.

20. The biosensor component according to claim 1, wherein said biosensor component has a sheet resistance of no more than 100 ohms per square.

* * * * *